US012808875B2

(12) United States Patent
Takeuchi et al.

(10) Patent No.: US 12,808,875 B2
(45) Date of Patent: Nov. 24, 2026

(54) CELL EVALUATION METHOD AND CELL EVALUATION DEVICE

(71) Applicant: HAMAMATSU PHOTONICS K.K., Hamamatsu (JP)

(72) Inventors: Kozo Takeuchi, Hamamatsu (JP); Osamu Yasuhiko, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 232 days.

(21) Appl. No.: 18/847,799

(22) PCT Filed: Mar. 16, 2023

(86) PCT No.: PCT/JP2023/010411
§ 371 (c)(1),
(2) Date: Sep. 17, 2024

(87) PCT Pub. No.: WO2023/182169
PCT Pub. Date: Sep. 28, 2023

(65) Prior Publication Data
US 2025/0216396 A1 Jul. 3, 2025

(30) Foreign Application Priority Data
Mar. 22, 2022 (JP) ................................ 2022-045496

(51) Int. Cl.
*G01N 33/58* (2006.01)
*G01N 21/31* (2006.01)

(52) U.S. Cl.
CPC ............ *G01N 33/58* (2013.01); *G01N 21/31* (2013.01)

(58) Field of Classification Search
CPC .............................. G01N 33/58; G01N 21/31
See application file for complete search history.

(56) References Cited

U.S. PATENT DOCUMENTS 9,405,958 B2 8/2016 Sugiyama et al.
2015/0177095 A1* 6/2015 Sugimoto .......... G01M 11/0271 356/517

FOREIGN PATENT DOCUMENTS

JP 2011-112548 A 6/2011
JP 2012-055267 A 3/2012
(Continued)

OTHER PUBLICATIONS

European Search Report for EP Patent Application No. 23774765.4, Issued on Feb. 19, 2026, 10 pages.
(Continued)

*Primary Examiner* — Jamil Ahmed
(74) *Attorney, Agent, or Firm* — Faegre Drinker Biddle & Reath LLP

(57) ABSTRACT

A cell evaluation method includes a labeling step, a refractive index distribution acquisition step, and an analysis step. In the labeling step, a specific component in a cell being an evaluation object is labeled with a labeling substance having refractive indices respectively at a first wavelength and a second wavelength different from each other. In the refractive index distribution acquisition step, a refractive index distribution of the cell in which the specific component is labeled in the labeling step is acquired at each of the first wavelength and the second wavelength. In the analysis step, a distribution of the specific component in the cell is evaluated by comparing the refractive index distributions respectively at the first wavelength and the second wavelength.

12 Claims, 41 Drawing Sheets

(56) References Cited

FOREIGN PATENT DOCUMENTS

| | | | |
|---|---|---|---|
| JP | 5745919 | B2 | 7/2015 |
| SE | 500817 | C2 | 9/1994 |
| WO | 1994/017393 | A1 | 8/1994 |
| WO | WO-2020/013325 | A1 | 1/2020 |
| WO | WO-2022/054305 | A1 | 3/2022 |

OTHER PUBLICATIONS

Rappaz et al., "Simultaneous cell morphometry and refractive index measurement with dual-wavelength digital holographic microscopy and dye-enhanced dispersion of perfusion medium", Optics Letters, vol. 33, No. 7, 2008, pp. 44-746.

Baczewska, M. et al., "Refractive Index Changes of Cells and Cellular Compartments Upon Paraformaldehyde Fixation Acquired by Tomographic Phase Microscopy," Cytometry Part A, vol. 99A, 2021, pp. 388-398.

Fu, D. et al., "Quantitative dispersion microscopy," Biomed. Opt. Express vol. 1, 2010, pp. 347-353.

Sai, T. et al., "Designing refractive index fluids using the Kramers-Kronig relations," Faraday Discussions vol. 223, 2020, pp. 136-144.

Yasuhiko, O. et al., "Single-shot quantitative phase imaging as an extension of differential interference contrast microscopy," Genes to Cells vol. 26, 2021, pp. 596-610.

Yasuhiko, O. et al., "Multiple-scattering suppressive refractive index tomography for the label-free quantitative assessment of multicellular spheroids," Biomed. Opt. Express vol. 13, 2022, pp. 962-979.

International Preliminary Report on Patentability mailed Oct. 3, 2024 for PCT/JP2023/010411.

* cited by examiner

*Fig.5*
(a)
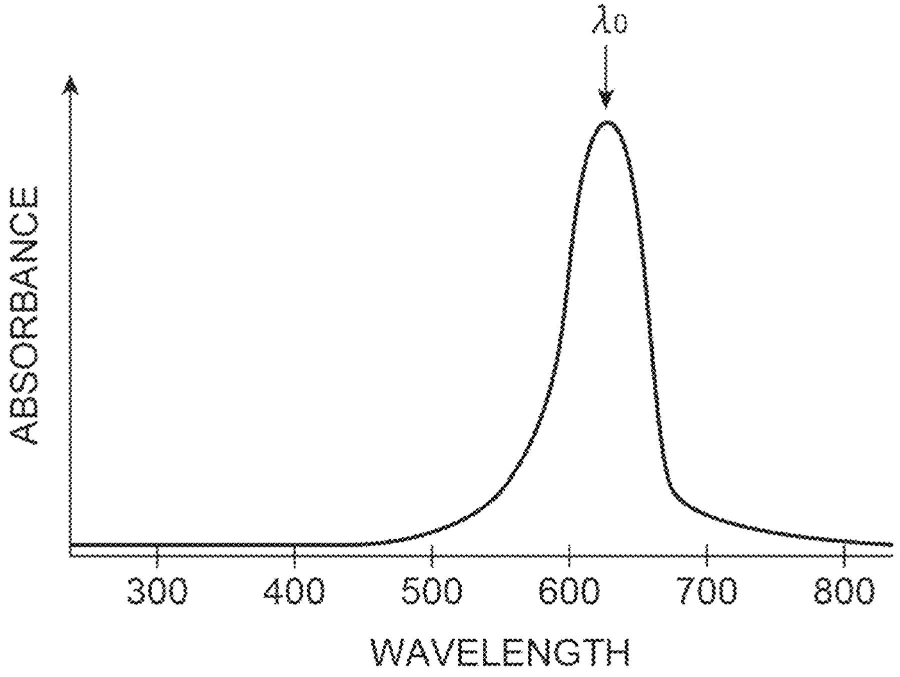
(b)
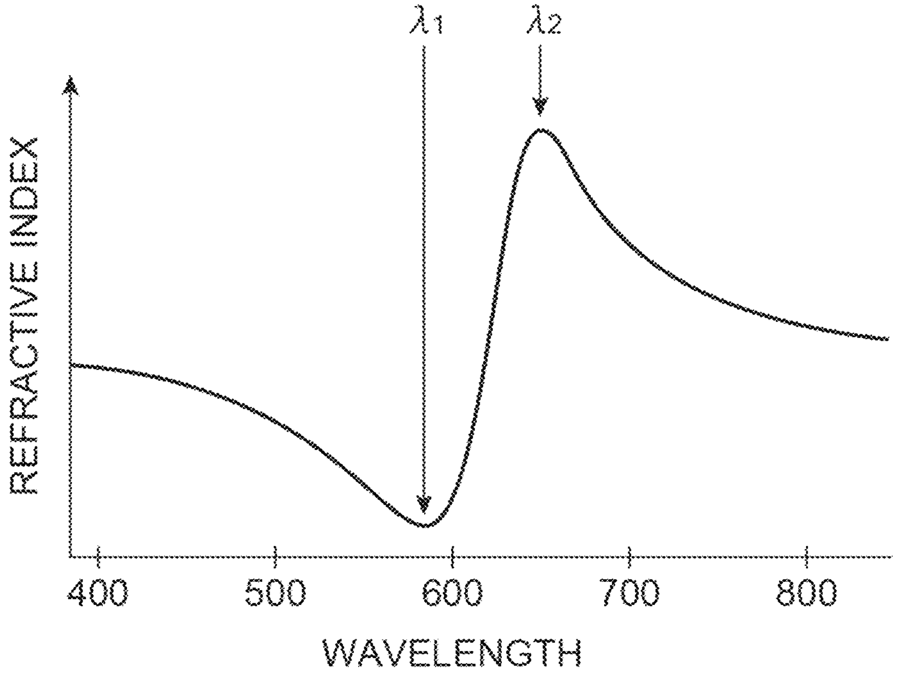

Fig.8
(a)
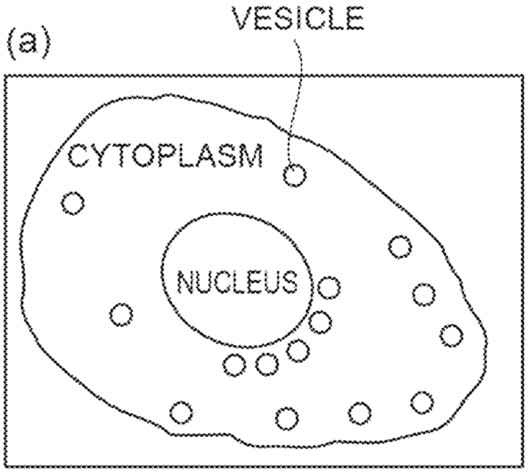
(b)
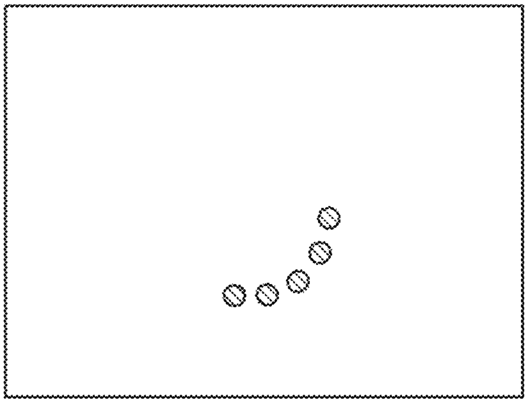
(c)
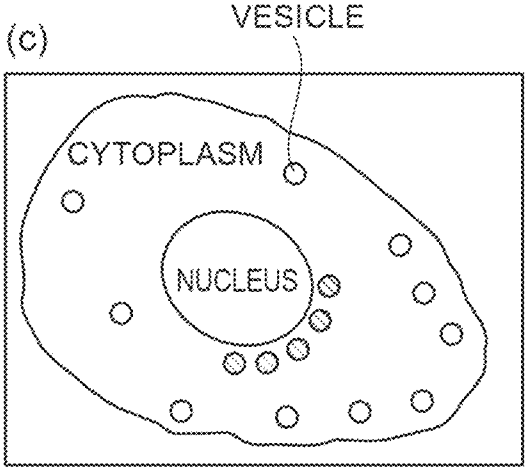

Fig.14
(a)
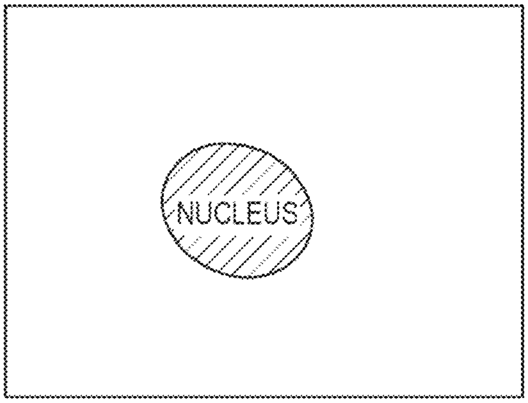
(b)
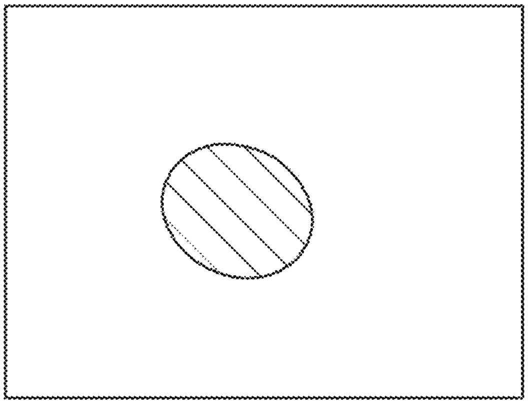
(c)
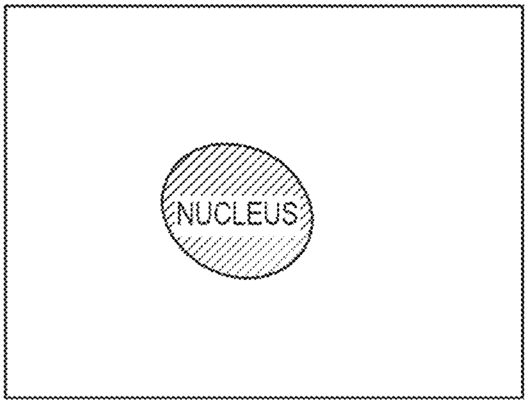

Fig.17
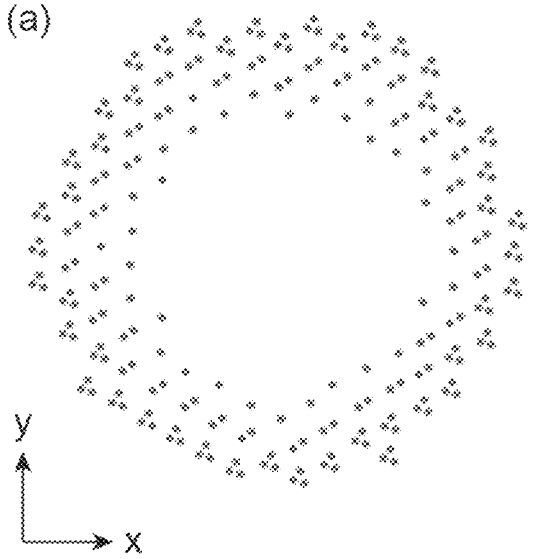
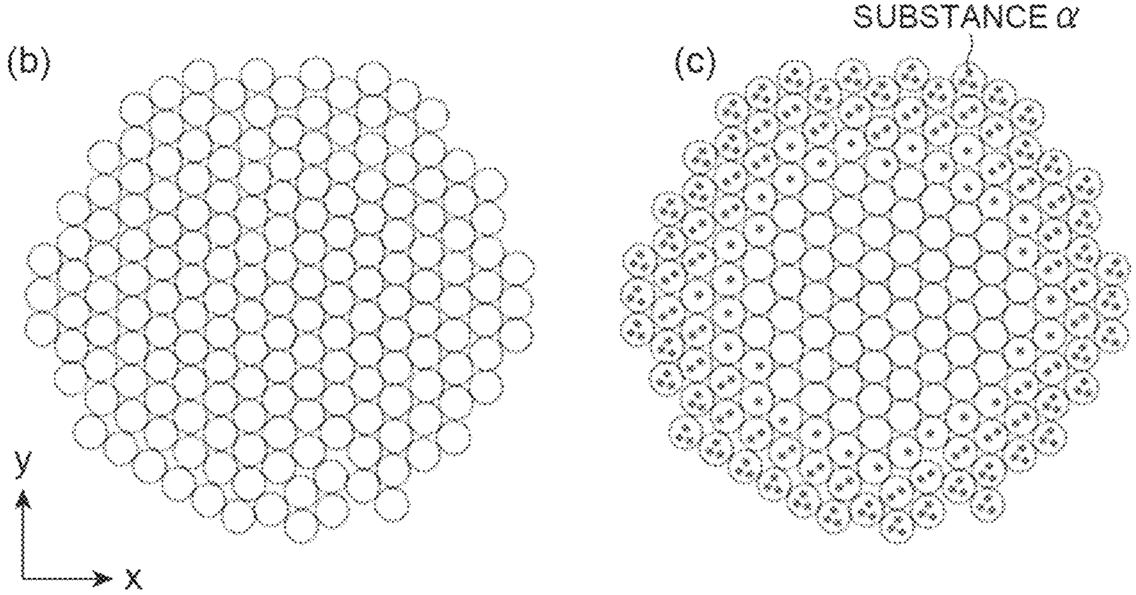

*Fig.19*

| | LIGHT ABSORBING LABELING SUBSTANCE | CENTER WAVELENGTH (nm) | | CELL |
|---|---|---|---|---|
| EXAMPLE 1A | Brilliant cresyl blue | 433 | 694 | A549 cell line |
| EXAMPLE 1B | Brilliant cresyl blue | 433 | 694 | HepG2 cell line |
| EXAMPLE 2A | New methylene blue | 530 | 694 | A549 cell line |
| EXAMPLE 2B | New methylene blue | 530 | 694 | HepG2 cell line |
| EXAMPLE 3 | Neutral red | 433 | 620 | HepG2 cell line |
| COMPARATIVE EXAMPLE 3 | (Not used) | 433 | 620 | HepG2 cell line |
| EXAMPLE 4 | Janus green B | 530 | 694 | A549 cell line |
| COMPARATIVE EXAMPLE 4 | (Not used) | 530 | 694 | A549 cell line |

Fig.24
(a)
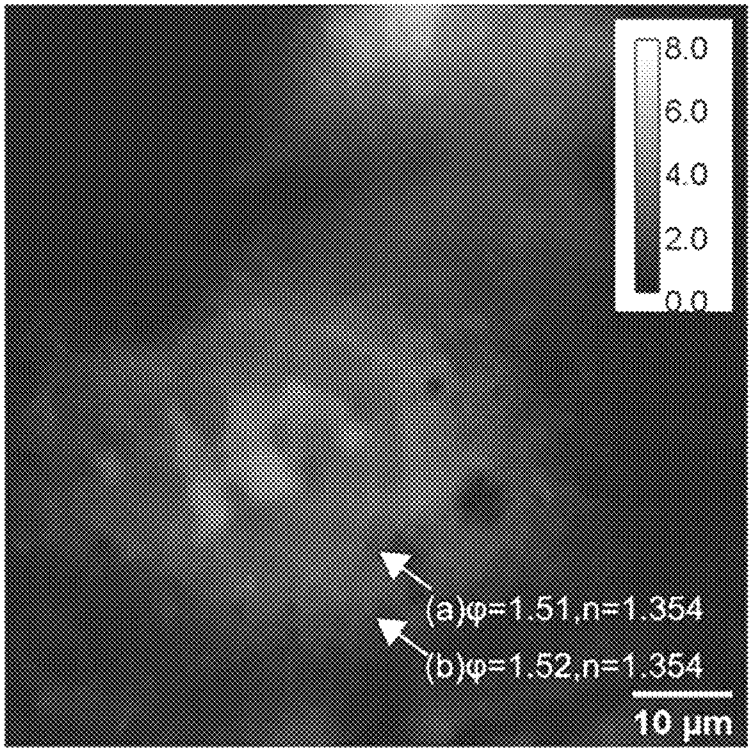
(b)
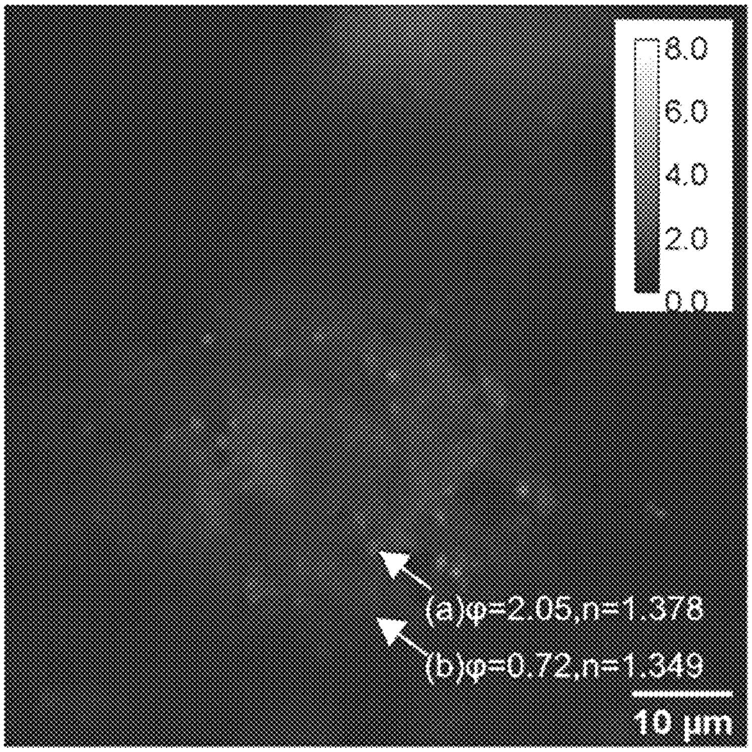

Fig.25
(a)
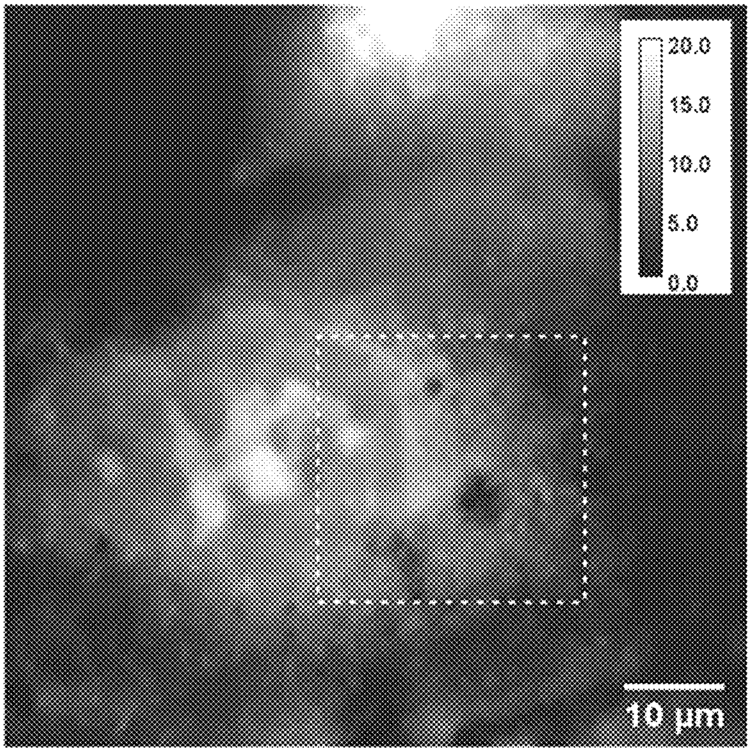
(b)
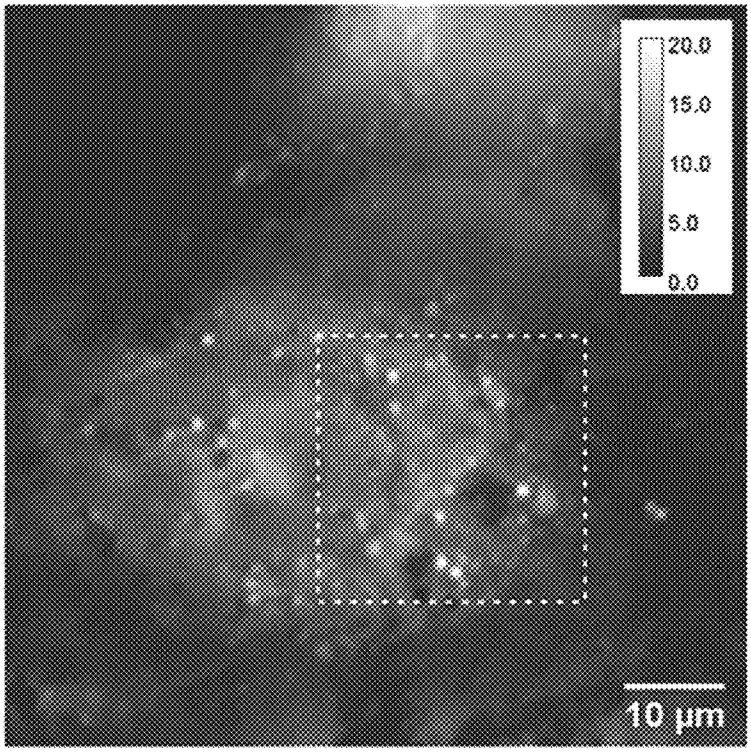

Fig.26
(a)
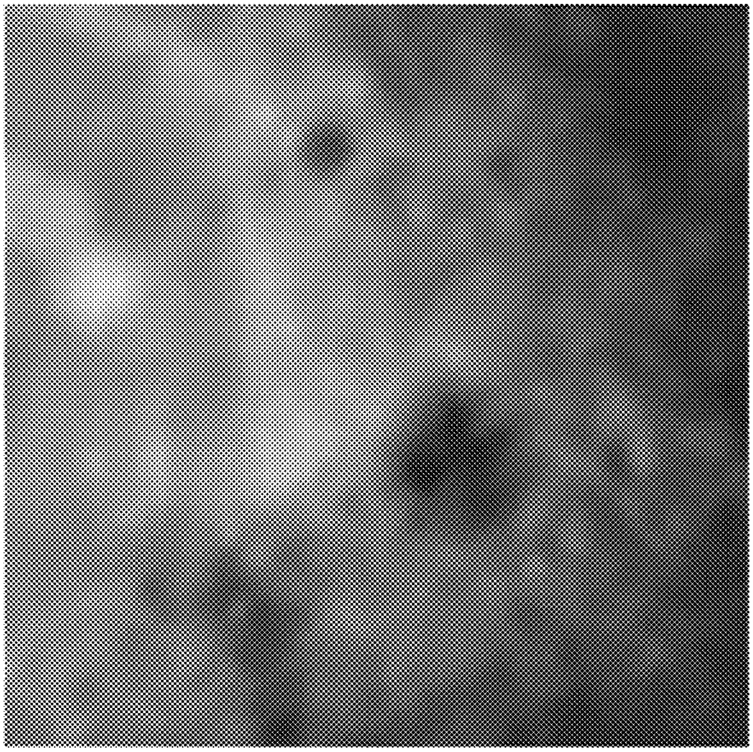
(b)
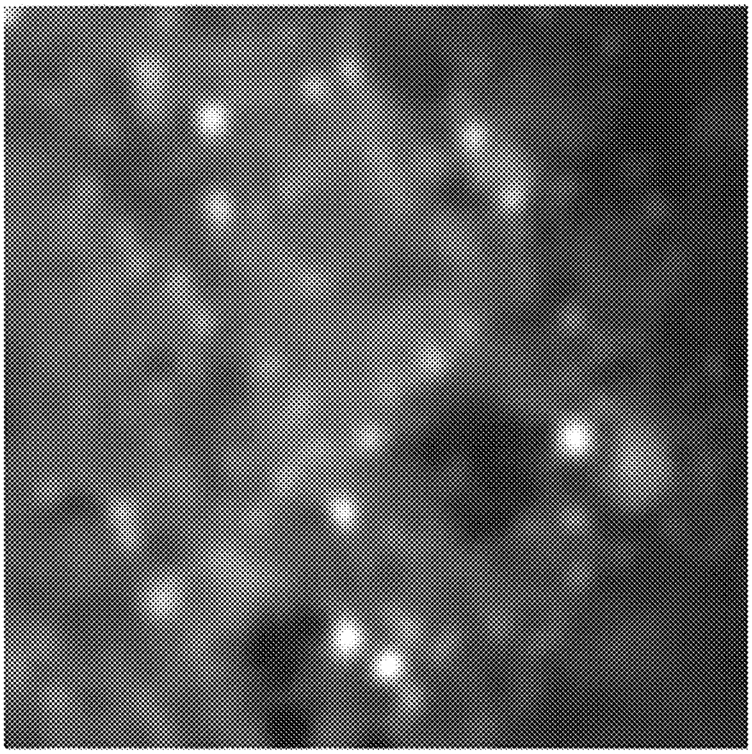

Fig.27
(a)
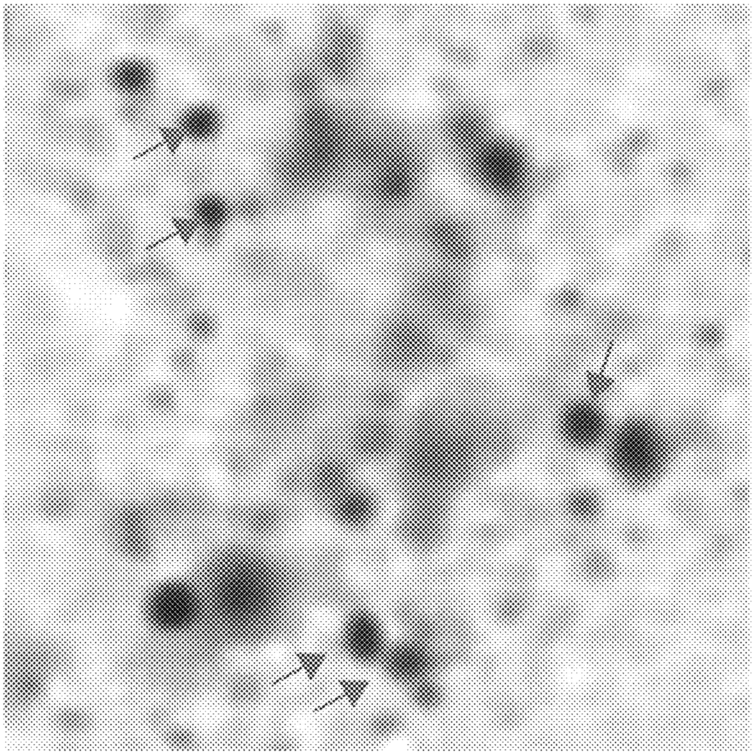
(b)
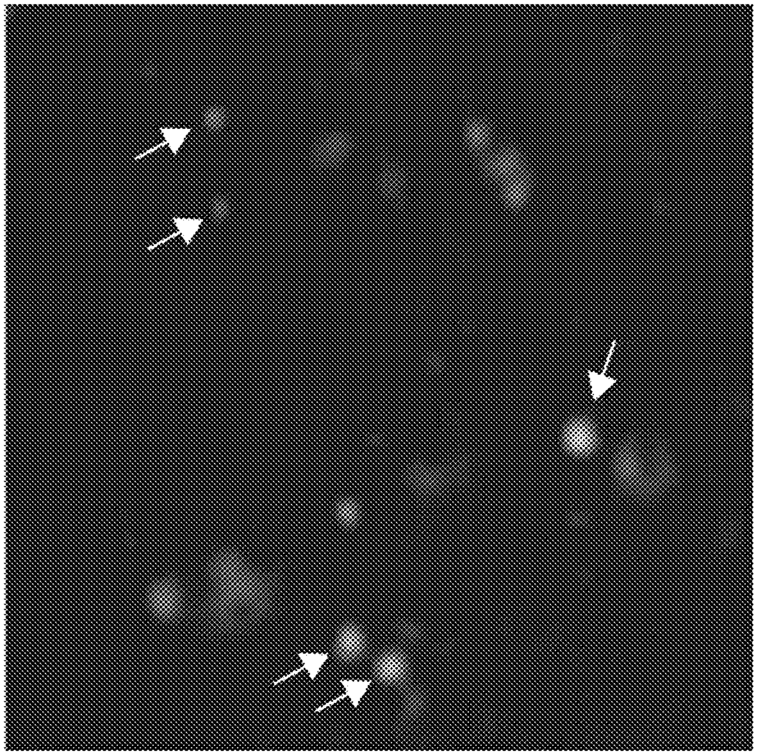

Fig.29
(a)
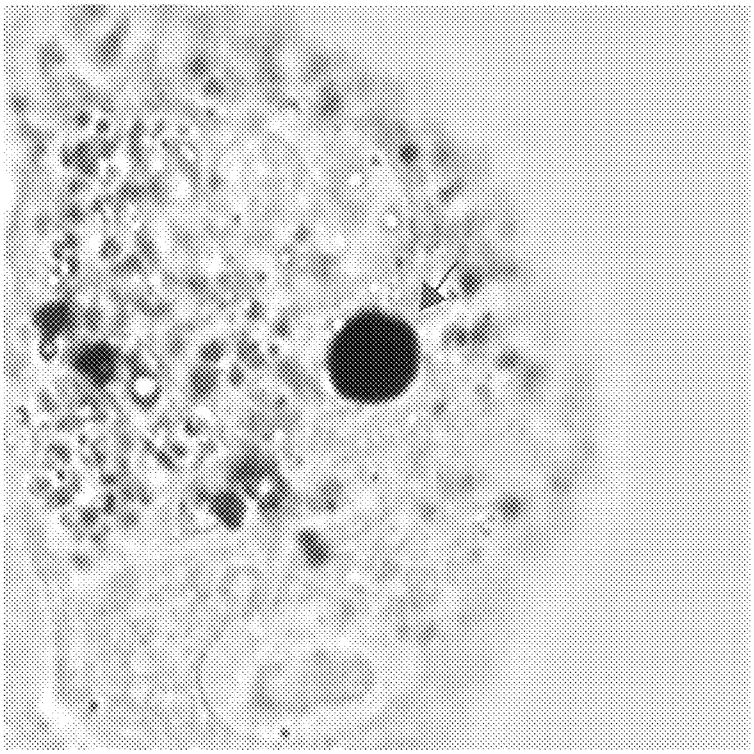
(b)
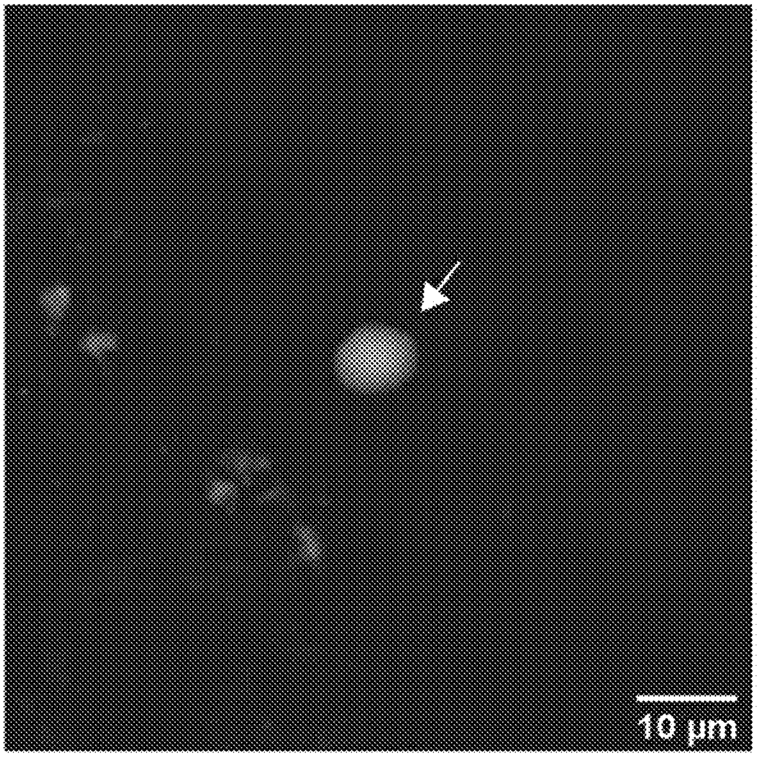

*Fig.30*
(a)
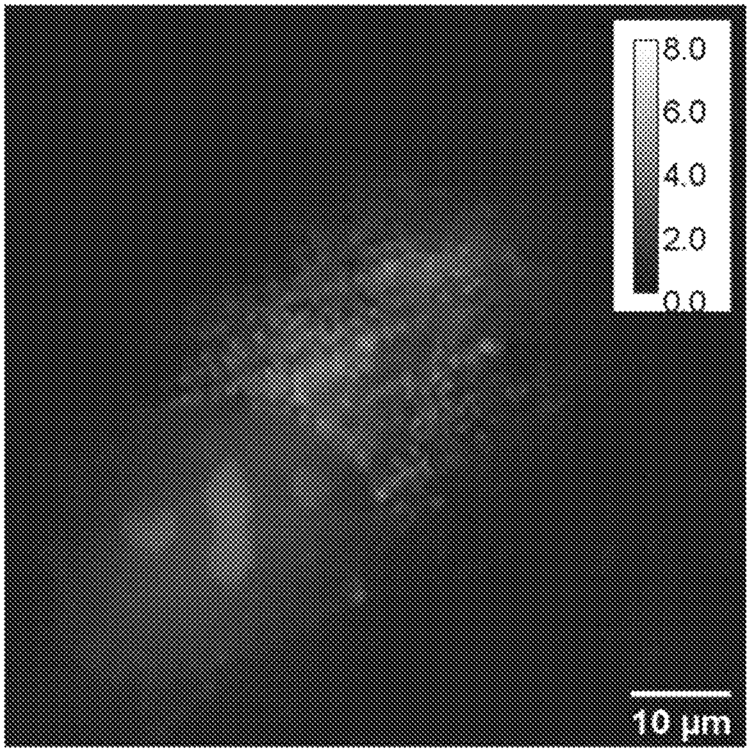
(b)
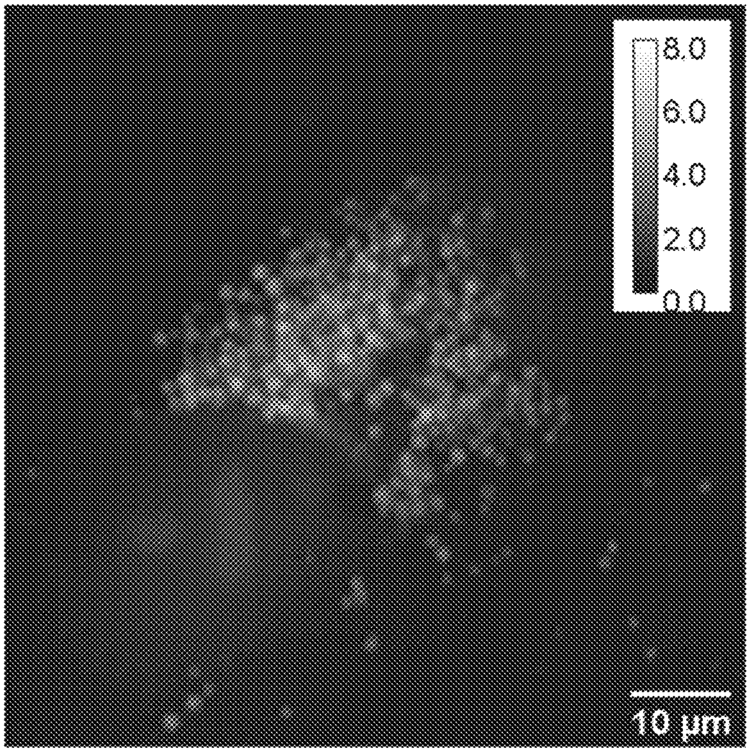

*Fig.31*
(a)
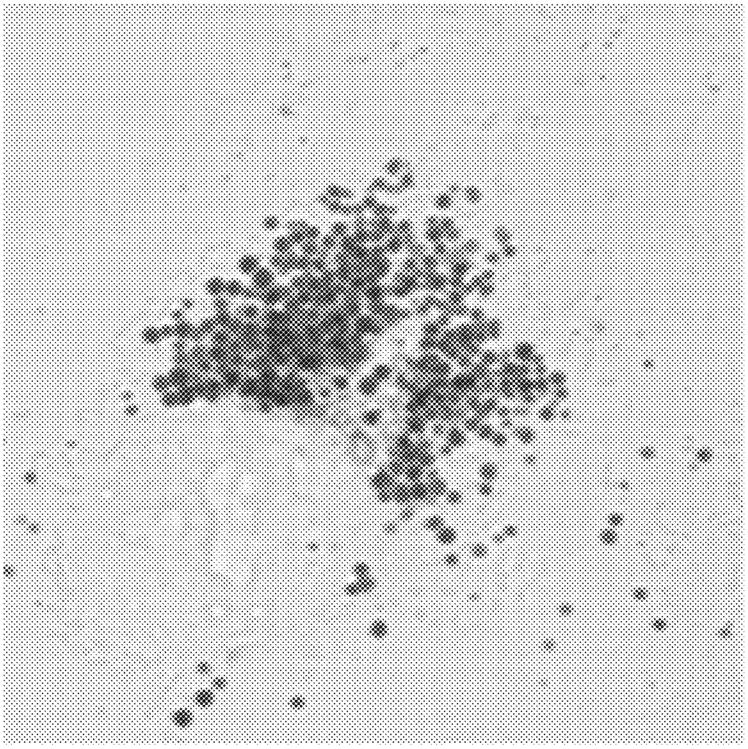
(b)
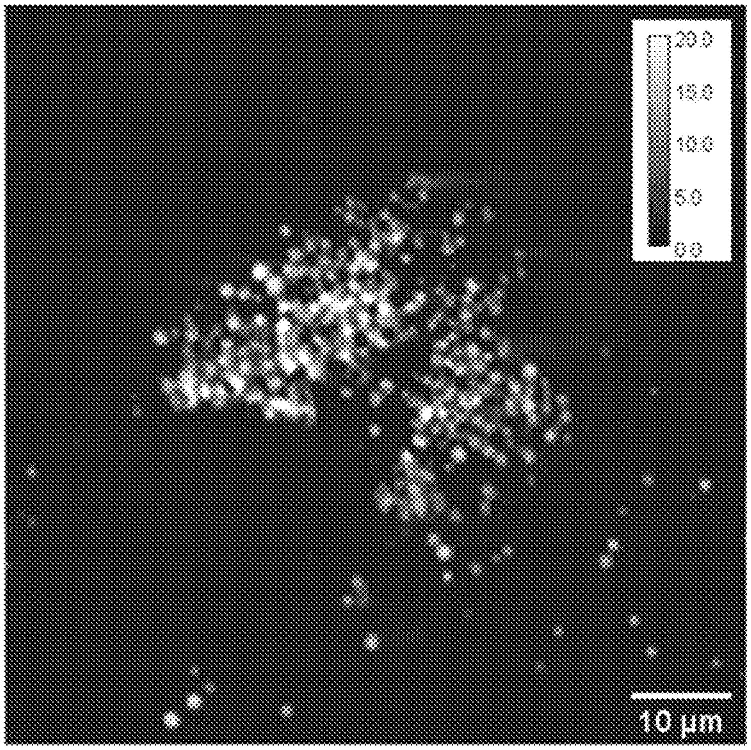

Fig.32
(a)
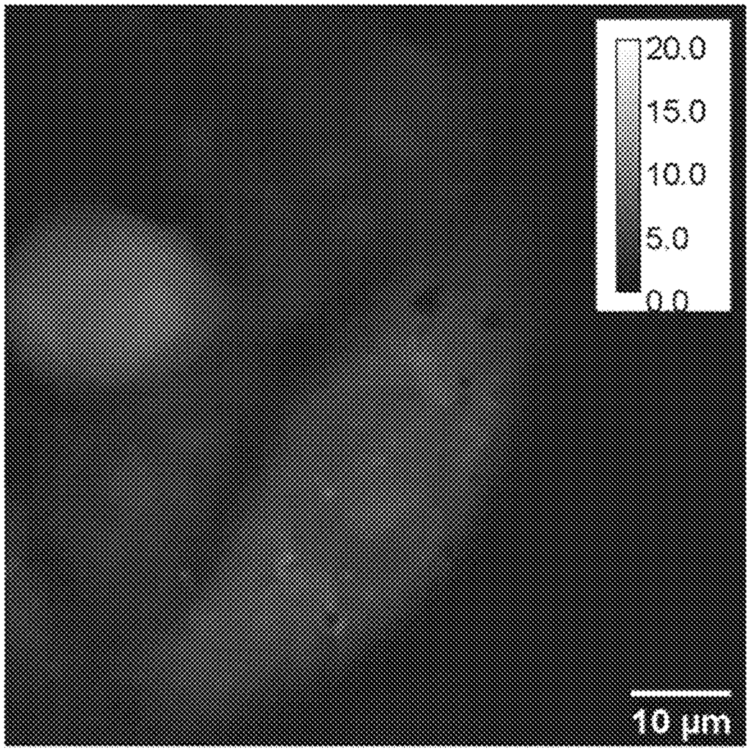
(b)
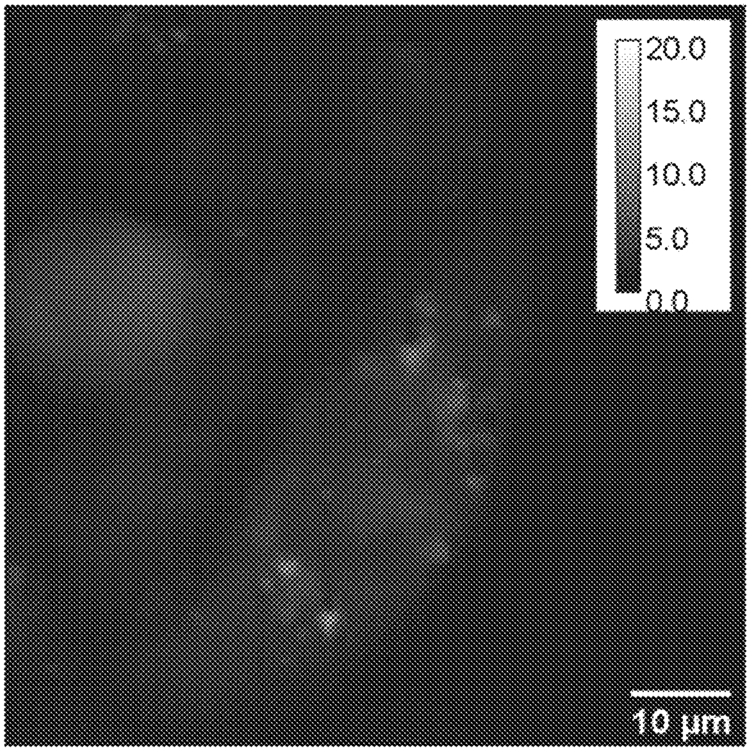

Fig.34
(a)
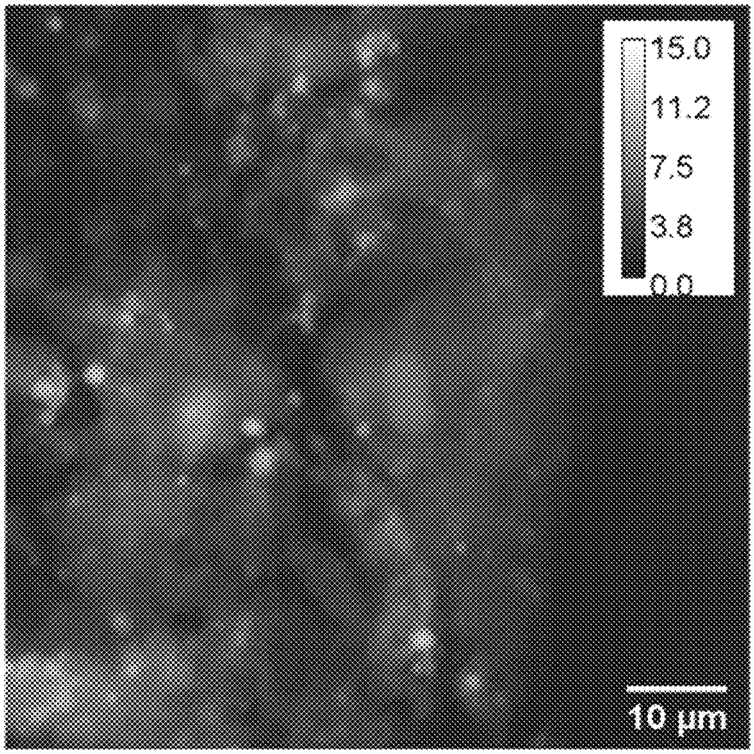
(b)
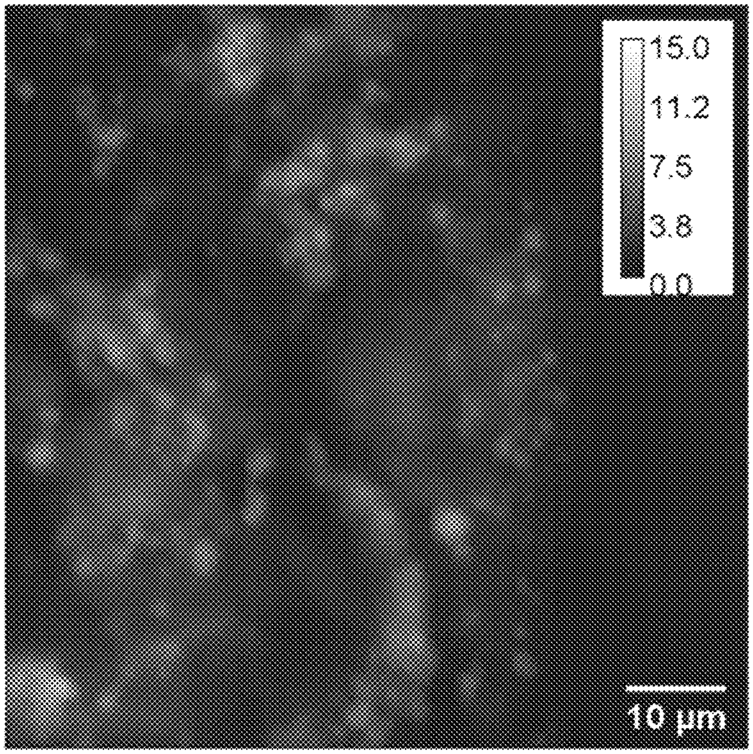

Fig.35
(a)
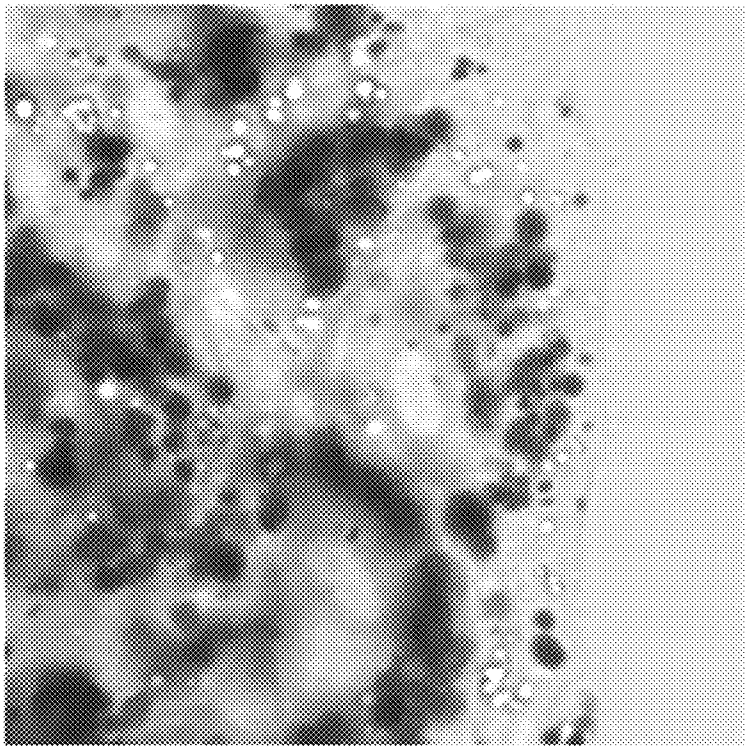
(b)
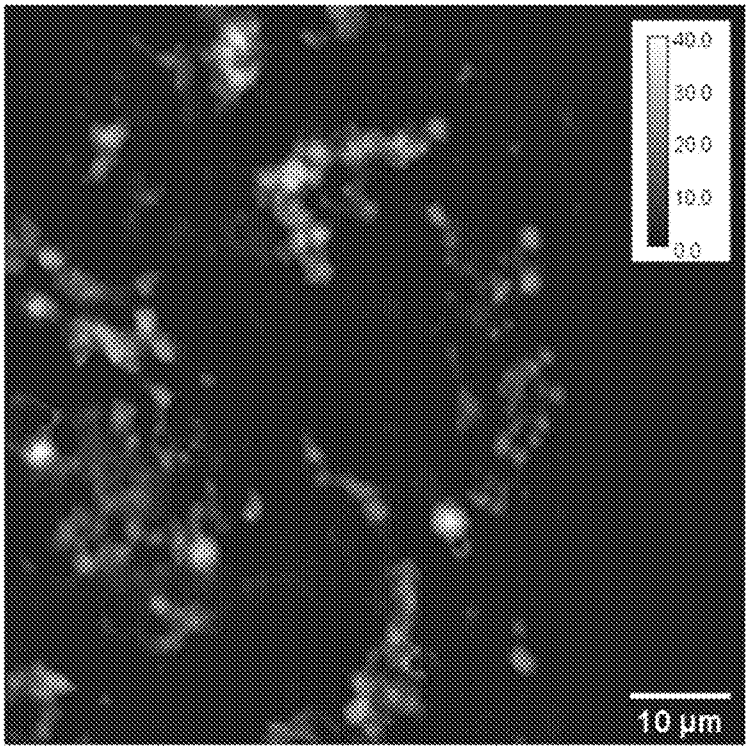

Fig.36
(a)
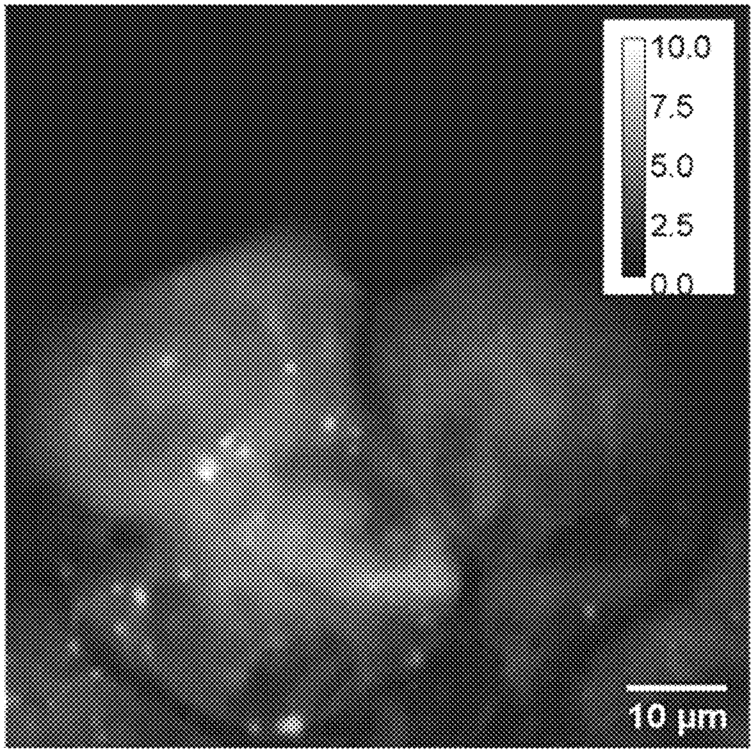
(b)
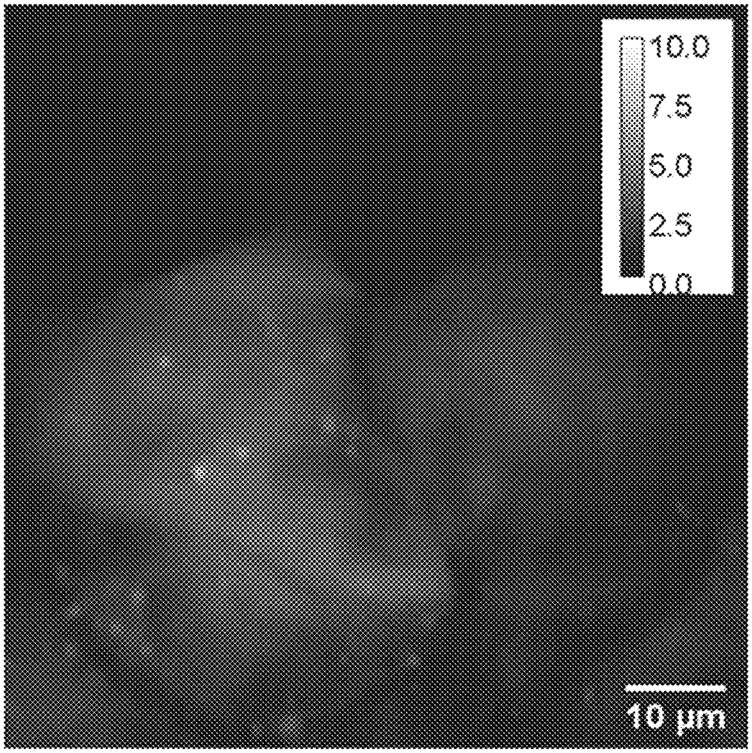

Fig.37
(a)
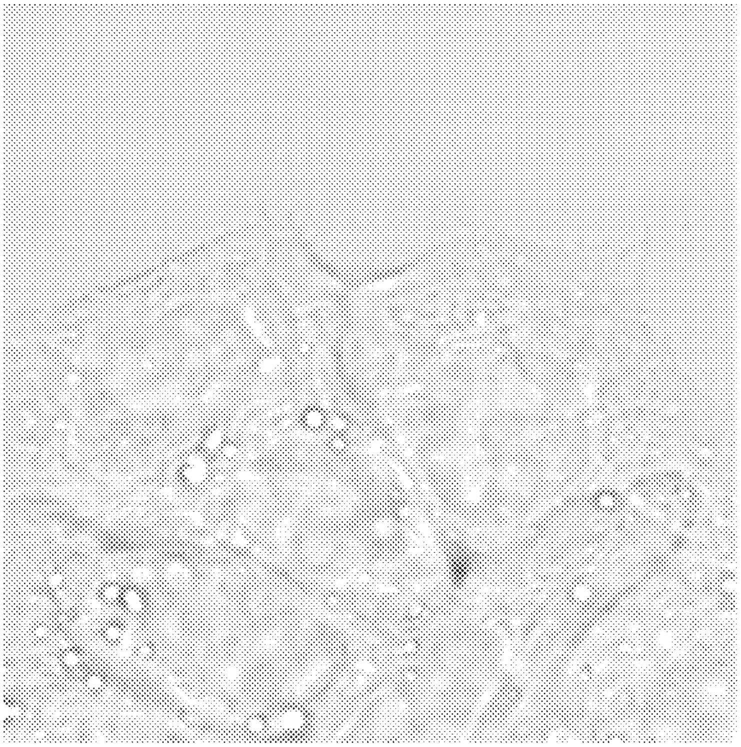
(b)
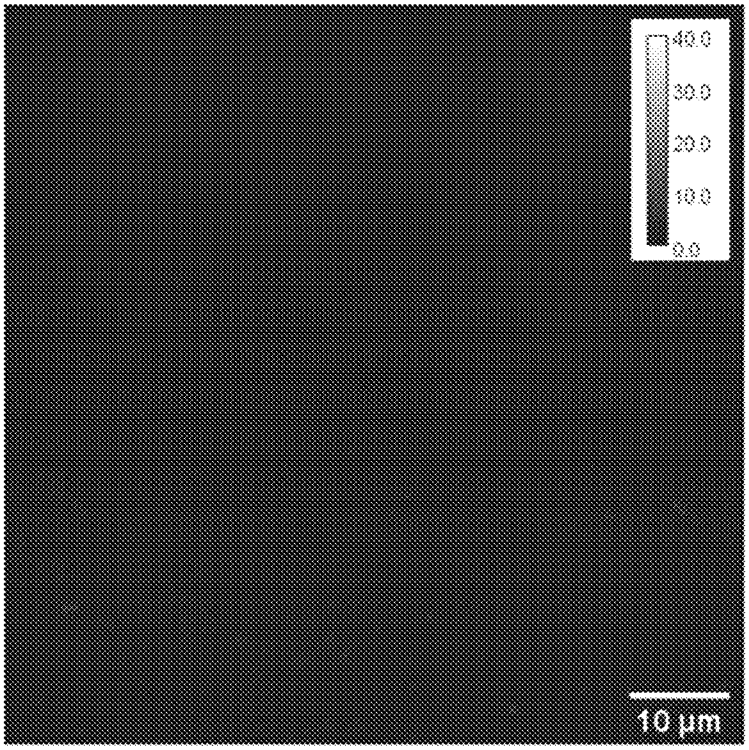

Fig.38
(a)
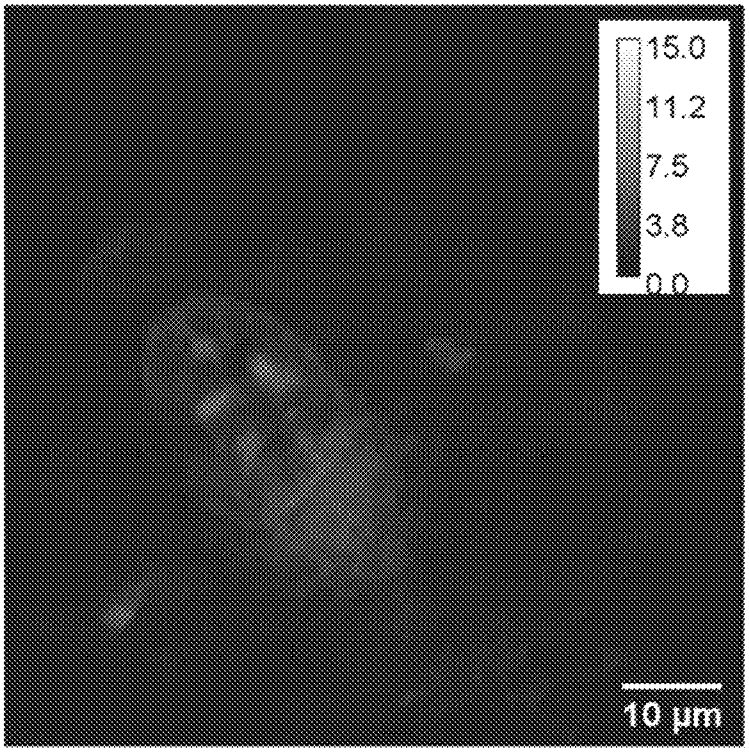
(b)
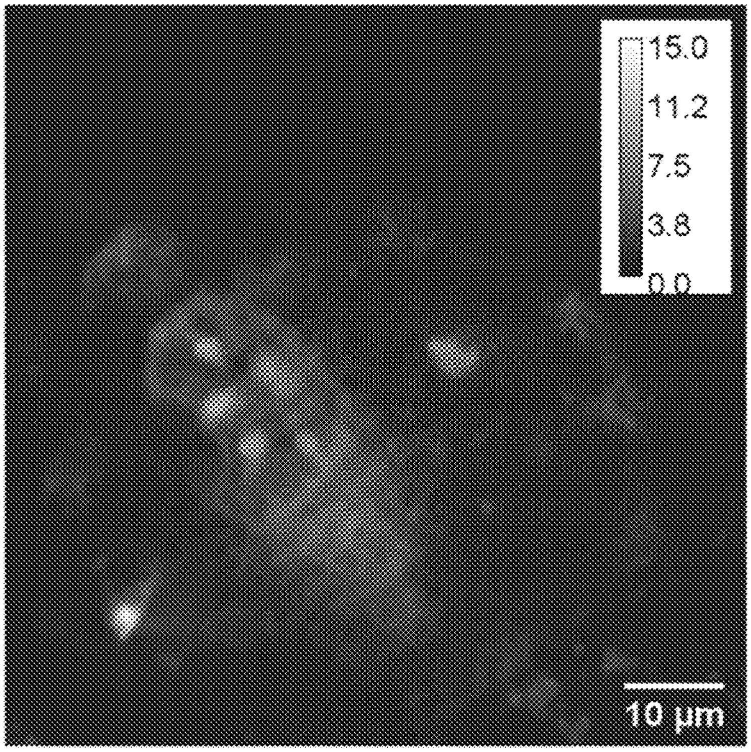

Fig.39
(a)
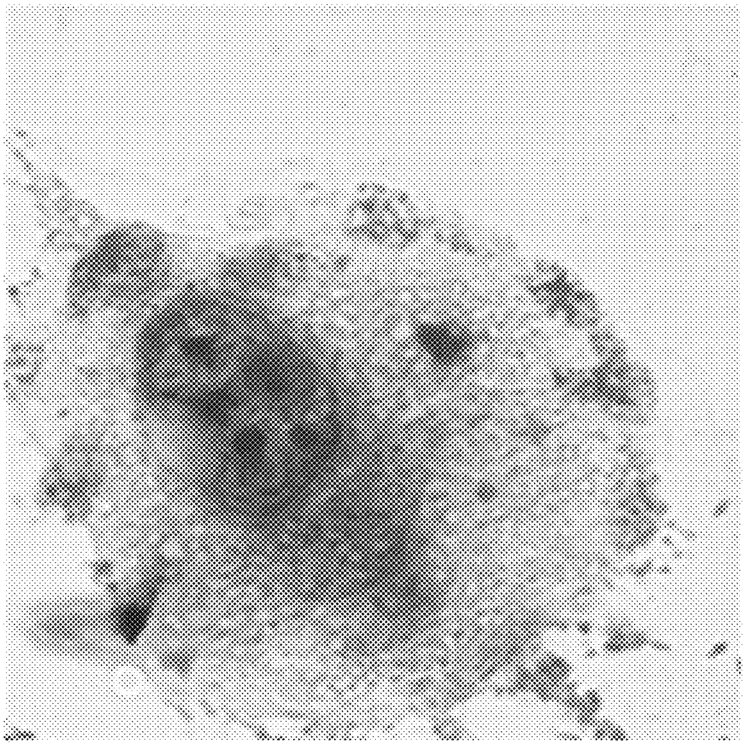
(b)
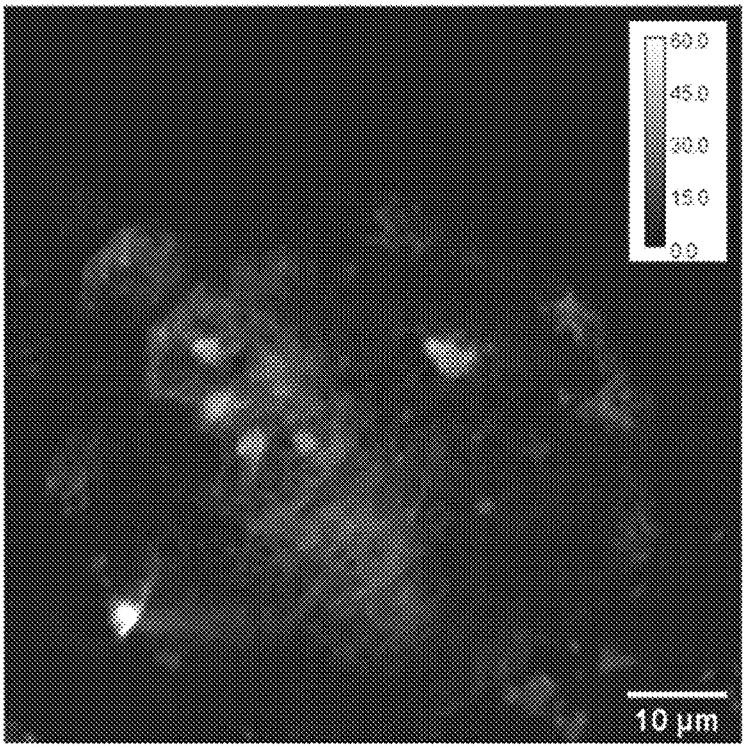

*Fig.40*
(a)
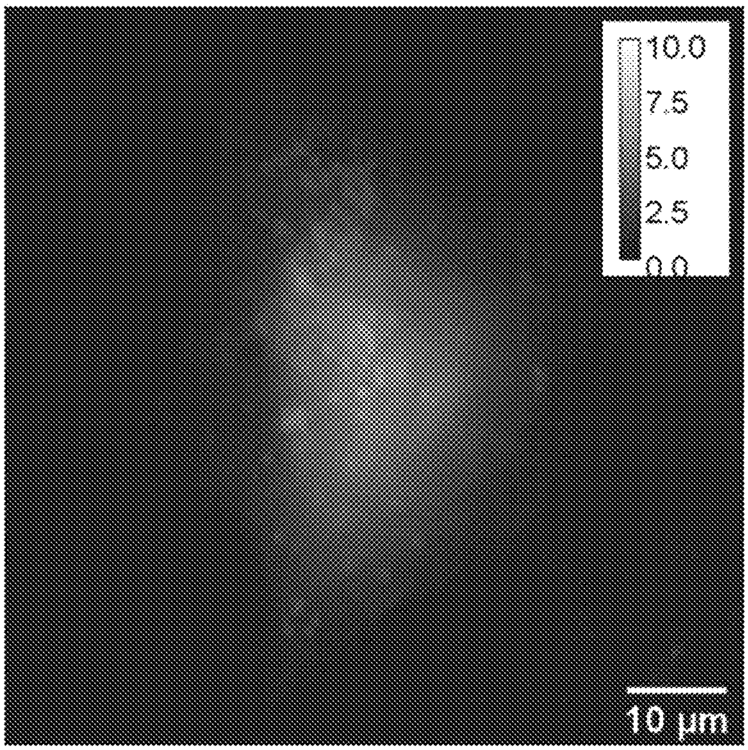
(b)
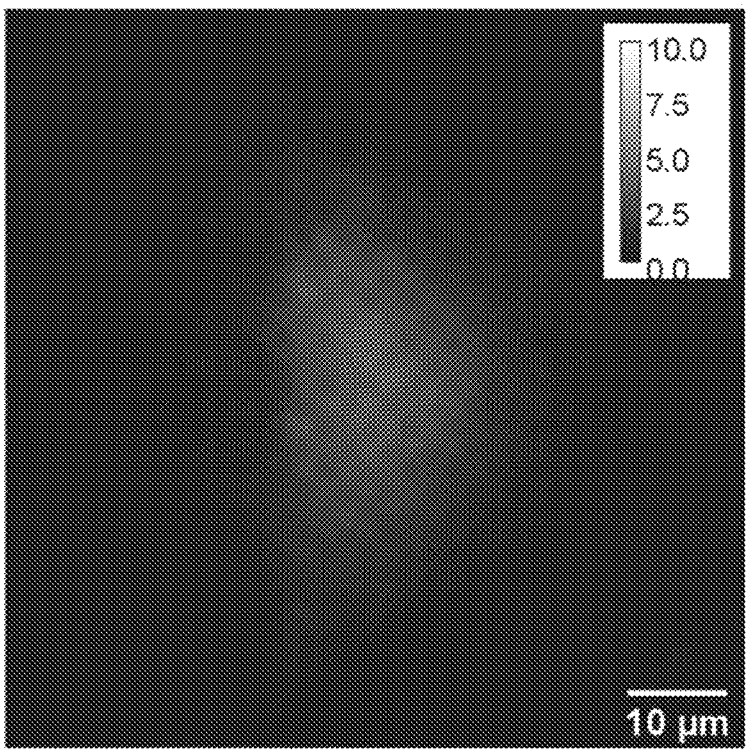

Fig.41
(a)
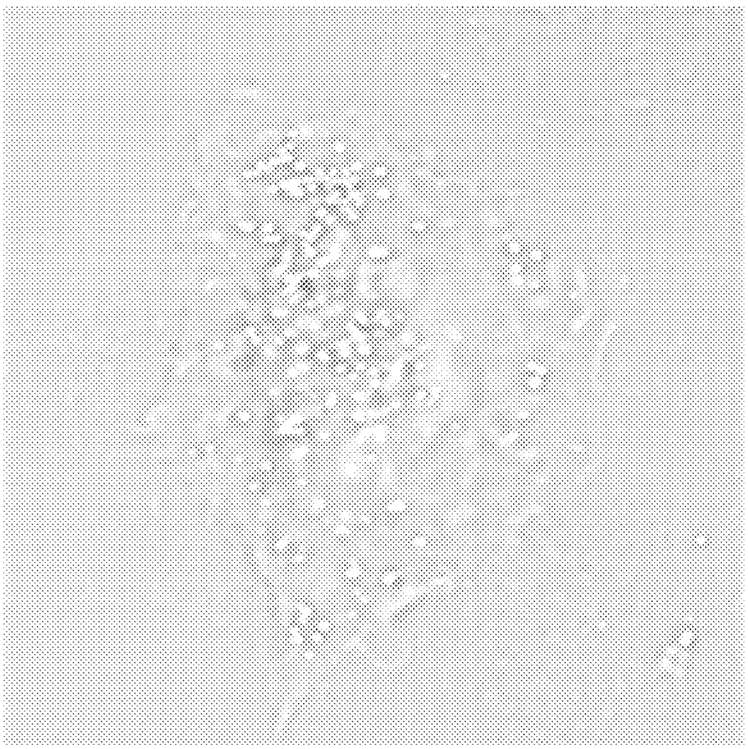
(b)
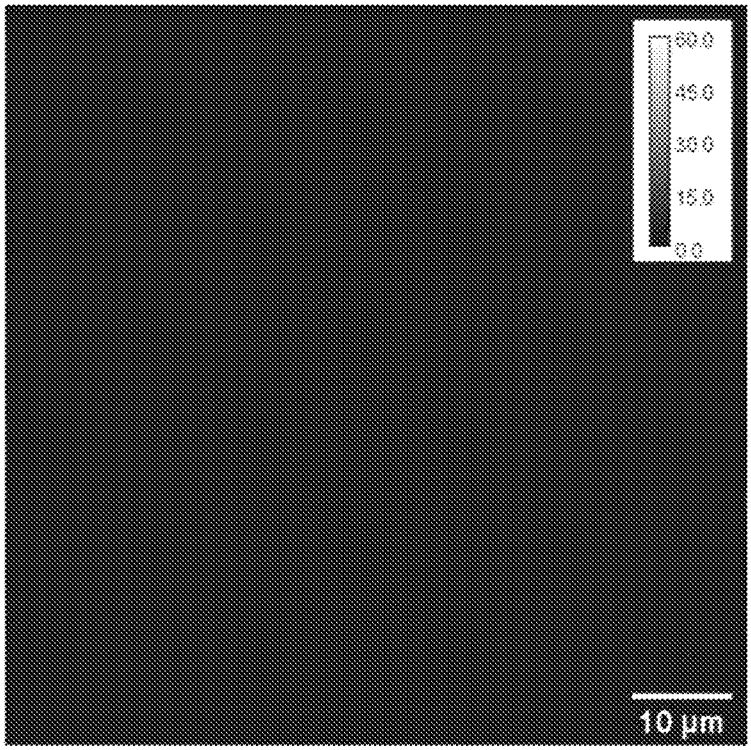

CELL EVALUATION METHOD AND CELL EVALUATION DEVICE

TECHNICAL FIELD

The present disclosure relates to a method and an apparatus for evaluating a distribution of a specific component in a cell.

BACKGROUND ART

It is difficult to observe a transparent observation object such as a cell, for example, by using a normal microscope, and thus, in general, an observation apparatus capable of acquiring a phase image or a refractive index distribution image of the observation object is used. Several methods for realizing the above observation apparatus are known.

One of the conventional techniques uses a Michelson interferometer or a Mach-Zehnder interferometer for performing splitting and combining of two light beams, and arranges the observation object on an optical path of one of the two light beams. Further, an optical path difference (a phase difference) between the two light beams is sequentially set to each value by moving a mirror or the like provided on the optical path, a plurality of interference images of the observation object are acquired, and a phase image of the observation object can be generated based on the plurality of interference images.

A technique described in Non Patent Document 1 uses a configuration in which a differential interference contrast microscope is combined with a quarter wave plate and a polarization camera. Further, a phase image of the observation object can be generated based on an interference image for each of a plurality of polarization components acquired by the polarization camera.

When a thickness of the observation object is set to d, a wavelength of the light is set to λ, and a refractive index is set to n, a phase ϕ is expressed by a relational expression of $\phi=2\pi \cdot n \cdot d/\lambda$. Therefore, when the thickness d and the wavelength λ are known, a refractive index distribution image can be generated from the phase image.

An optical diffraction tomography (ODT) technique described in Non Patent Document 2 uses a Mach-Zehnder interferometer for performing splitting and combining of two light beams, and arranges the observation object on an optical path of one of the two light beams. Further, a light incident direction on the observation object is variously set to acquire a plurality of interference images of the observation object, and further, a refractive index distribution image of the observation object can be generated based on the plurality of interference images.

Patent Document 1 discloses an invention for evaluating a stem cell based on a phase image. The invention disclosed in this document compares a phase of a portion of a cell nucleus and a phase of a portion of a cytoplasm in the phase image of the stem cell, and evaluates a quality of the stem cell based on the comparison result.

CITATION LIST

Patent Literature

Patent Document 1: Japanese Patent Publication No. 5745919

Non Patent Literature

Non Patent Document 1: O. Yasuhiko, K. Takeuchi, H. Yamada, and Y. Ueda, "Single-shot quantitative phase imaging as an extension of differential interference contrast microscopy", Genes to Cells Vol. 26, pp. 596-610, 2021

Non Patent Document 2: O. Yasuhiko, K. Takeuchi, H. Yamada, and Y. Ueda, "Multiple-scattering suppressive refractive index tomography for the label-free quantitative assessment of multicellular spheroids", Biomed. Opt. Express Vol. 13, pp. 962-979, 2022

Non Patent Document 3: D. Fu et al., "Quantitative dispersion microscopy", Biomed. Opt. Express Vol. 1, pp. 347-353, 2010

Non Patent Document 4: T. Sai et al., "Designing refractive index fluids using the Kramers-Kronig relations", Faraday Discussions Vol. 223, pp. 136-144, 2020

SUMMARY OF INVENTION

Technical Problem

When a type of the cell is known, it is possible to evaluate the cell (for example, evaluate a quality of the cell) based on the phase image or the refractive index distribution image of the cell acquired by the conventional technique described above. However, in the case in which the type of the cell is unknown, the phase image and the refractive index distribution image of the cell acquired by the above conventional technique may not clearly represent any information of the cell, and thus, it is difficult to evaluate the cell based on the above images.

An object of an embodiment is to provide a method and an apparatus capable of easily evaluating a cell even in the case in which the cell is an unknown cell.

Solution to Problem

An embodiment is a cell evaluation method. The cell evaluation method includes a labeling step of labeling a specific component in a cell with a labeling substance having refractive indices respectively at a first wavelength and a second wavelength different from each other; a refractive index distribution acquisition step of acquiring a refractive index distribution of the cell in which the specific component is labeled in the labeling step at each of the first wavelength and the second wavelength; and an analysis step of evaluating a distribution of the specific component in the cell by comparing the refractive index distributions respectively at the first wavelength and the second wavelength.

An embodiment is a cell evaluation apparatus. The cell evaluation apparatus includes a refractive index distribution acquisition unit for acquiring a refractive index distribution of a cell in which a specific component is labeled with a labeling substance having refractive indices respectively at a first wavelength and a second wavelength different from each other at each of the first wavelength and the second wavelength; and an analysis unit for evaluating a distribution of the specific component in the cell by comparing the refractive index distributions respectively at the first wavelength and the second wavelength.

An embodiment is a program. The program is a program for causing a computer to execute a refractive index distribution acquisition step of acquiring a refractive index distribution of a cell in which a specific component is labeled with a labeling substance having refractive indices respectively at a first wavelength and a second wavelength different from each other at each of the first wavelength and the second wavelength; and an analysis step of evaluating a distribution of the specific component in the cell by comparing the refractive index distributions respectively at the first wavelength and the second wavelength.

Advantageous Effects of Invention

According to the cell evaluation method and the cell evaluation apparatus of the embodiments, a call can be easily evaluated even in the case in which the cell is an unknown cell.

BRIEF DESCRIPTION OF DRAWINGS

FIG. 5 includes diagrams schematically showing a light absorption spectrum and a refractive index spectrum of a light absorbing labeling substance, and shows (a) the light absorption spectrum, and (b) the refractive index spectrum.

FIG. 8 includes diagrams describing a first analysis example in an analysis step S3, and shows (a) a diagram schematically showing a refractive index distribution image, (b) a diagram schematically showing a refractive index variation image, and (c) a diagram in which the refractive index distribution image ((a) in FIG. 8) and the refractive index variation image ((b) in FIG. 8) are superimposed.

FIG. 14 includes diagrams describing a fifth analysis example in the analysis step S3, and shows (a) a diagram schematically showing the fluorescence image or the intensity image of the cell nucleus, (b) a diagram schematically showing the refractive index variation image acquired by labeling by using the labeling substance for an unknown labeling object, and (c) a diagram in which the fluorescence image or the intensity image of the cell nucleus ((a) in FIG. 14) and the refractive index variation image ((b) in FIG. 14) are superimposed.

FIG. 17 includes diagrams describing a seventh analysis example in the analysis step S3, and shows (a) a diagram schematically showing the refractive index variation image acquired by labeling the specific component in each of the cells included in the cell mass with the labeling substance α, (b) a diagram schematically showing the refractive index distribution image, and (c) a diagram in which the refractive index variation image ((a) in FIG. 17) and the refractive index distribution image ((b) in FIG. 17) are superimposed.

FIG. 19 is a table showing a light absorbing labeling substance, a center wavelength, and a cell used in each of examples.

FIG. 24 includes respective images of an example 1A, and shows (a) a phase image at the center wavelength of 433 nm, and (b) the phase image at the center wavelength of 694 nm.

FIG. 25 includes respective images of the example 1A, and shows (a) the refractive index distribution image at the center wavelength of 433 nm, and (b) the refractive index distribution image at the center wavelength of 694 nm.

FIG. 26 includes respective images of the example 1A, and shows (a) an enlarged diagram of a range indicated by a dashed line rectangle in (a) in FIG. 25, and (b) an enlarged diagram of a range indicated by a dashed line rectangle in (b) in FIG. 25.

FIG. 27 includes respective images of the example 1A, and shows (a) the intensity image at the center wavelength of 530 nm, and (b) the refractive index variation image.

FIG. 29 includes respective images of the example 1B, and shows (a) the intensity image at the center wavelength of 530 nm, and (b) the refractive index variation image.

FIG. 30 includes respective images of an example 2A, and shows (a) the phase image at the center wavelength of 530 nm, and (b) the phase image at the center wavelength of 694 nm.

FIG. 31 includes respective images of the example 2A, and shows (a) the intensity image at the center wavelength of 530 nm, and (b) the refractive index variation image.

FIG. 32 includes respective images of an example 2B, and shows (a) the phase image at the center wavelength of 530 nm, and (b) the phase image at the center wavelength of 694 nm.

FIG. 34 includes respective images of an example 3, and shows (a) the phase image at the center wavelength of 433 nm, and (b) the phase image at the center wavelength of 620 nm.

FIG. 35 includes respective images of the example 3, and shows (a) the intensity image at the center wavelength of 530 nm, and (b) the refractive index variation image.

FIG. 36 includes respective images of a comparative example 3, and shows (a) the phase image at the center wavelength of 433 nm, and (b) the phase image at the center wavelength of 620 nm.

FIG. 37 includes respective images of the comparative example 3, and shows (a) the intensity image at the center wavelength of 530 nm, and (b) the refractive index variation image.

FIG. 38 includes respective images of an example 4, and shows (a) the phase image at the center wavelength of 530 nm, and (b) the phase image at the center wavelength of 694 nm.

FIG. 39 includes respective images of the example 4, and shows (a) the intensity image at the center wavelength of 530 nm, and (b) the refractive index variation image.

FIG. 40 includes respective images of a comparative example 4, and shows (a) the phase image at the center wavelength of 530 nm, and (b) the phase image at the center wavelength of 694 nm.

FIG. 41 includes respective images of the comparative example 4, and shows (a) the intensity image at the center wavelength of 530 nm, and (b) the refractive index variation image.

DESCRIPTION OF EMBODIMENTS

Hereinafter, embodiments of a cell evaluation method and a cell evaluation apparatus will be described in detail with reference to the accompanying drawings. In the description of the drawings, the same elements will be denoted by the same reference signs, and redundant description will be omitted. The present invention is not limited to these examples, and the Claims, their equivalents, and all the changes within the scope are intended as would fall within the scope of the present invention.

Figure 1:
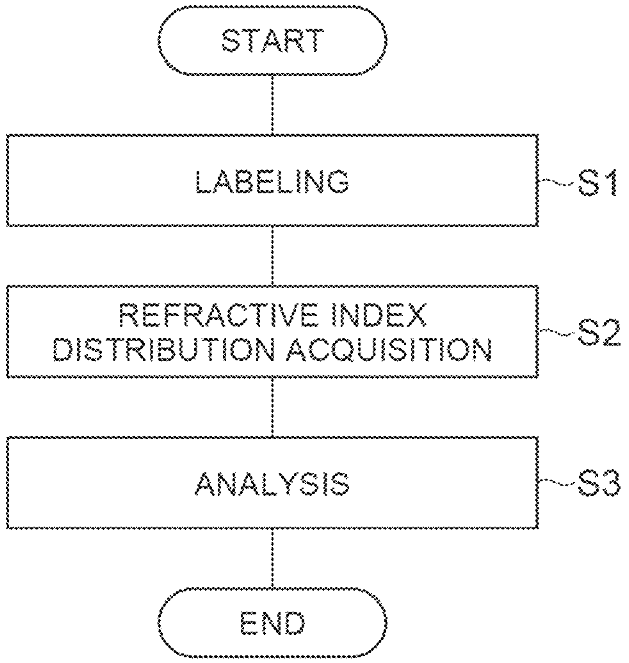
FIG. 1 is a flowchart of a cell evaluation method.

FIG. 1 is a flowchart of a cell evaluation method. The cell evaluation method includes a labeling step S1, a refractive index distribution acquisition step S2, and an analysis step S3. In the labeling step S1, a specific component in a cell, which is an evaluation object, is labeled with a labeling substance having refractive indices different from each other respectively at a first wavelength and a second wavelength.

In the refractive index distribution acquisition step S2, a refractive index distribution of the cell in which the specific component is labeled in the labeling step S1 is acquired at each of the first wavelength and the second wavelength. In the analysis step S3, a distribution of the specific component in the cell is evaluated by comparing the refractive index distributions respectively at the first wavelength and the second wavelength.

A cell evaluation apparatus capable of performing the respective processes of the refractive index distribution acquisition step S2 and the analysis step S3 in the cell evaluation method described above can be configured by using the technique described in, for example, Non Patent Document 1 or Non Patent Document 2.

Figure 2:
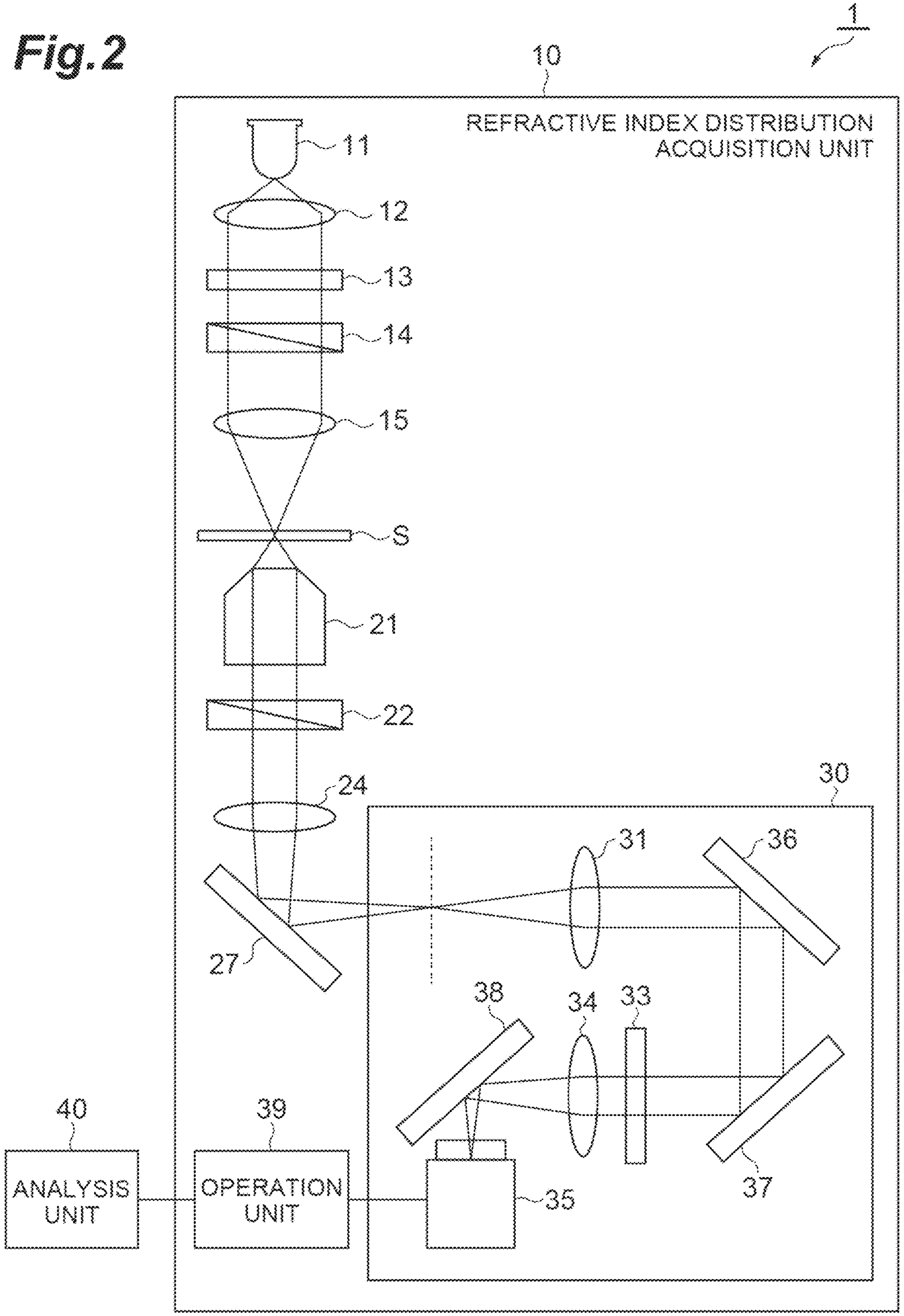
FIG. 2 is a diagram illustrating a configuration of a cell evaluation apparatus 1.

FIG. 2 is a diagram illustrating a configuration of a cell evaluation apparatus 1. The cell evaluation apparatus 1 includes a refractive index distribution acquisition unit 10 and an analysis unit 40. The refractive index distribution acquisition unit 10 performs the processing of the refractive index distribution acquisition step S2, and is configured based on the technique described in Non Patent Document 1. The analysis unit 40 performs the processing of the analysis step S3.

The refractive index distribution acquisition unit 10 includes a light source 11, a lens 12, a polarizer 13, a first prism 14, a condenser lens 15, an objective lens 21, a second prism 22, a lens 24, a mirror 27, an optical module 30, and an operation unit 39. The optical module 30 includes a lens 31, a quarter wave plate 33, a lens 34, a polarization camera 35, and mirrors 36 to 38.

A configuration of the refractive index distribution acquisition unit 10 excluding the optical module 30 and the operation unit 39 can be set to the same configuration as a configuration of a differential interference contrast microscope. That is, the refractive index distribution acquisition unit 10 can be configured by attaching the optical module 30 to a camera port of the differential interference contrast microscope, and further, providing the operation unit 39.

The lens 12, the polarizer 13, the first prism 14, and the condenser lens 15 are sequentially provided on an optical path of an irradiation optical system for focusing light output from the light source 11 and irradiating an evaluation object S with the light. Further, the objective lens 21, the second prism 22, the lens 24, the lens 31, the quarter wave plate 33, and the lens 34 are sequentially provided on an optical path of an imaging optical system for inputting light generated in the evaluation object S in response to irradiation of the evaluation object S with the light by the irradiation optical system and forming an image on an imaging plane of the polarization camera 35.

The light source 11 outputs spatially incoherent light. The light output from the light source 11 may be temporally coherent or may be temporally incoherent. The light output from the light source 11 may be linearly polarized light or may be unpolarized light. The light source 11 includes, for example, a halogen lamp, a light emitting diode, or a laser diode, and further, preferably includes a diffuser plate at a subsequent stage thereof.

The light source 11 can output light beams having center wavelengths different from each other. For example, the wavelength of the output light may be made variable by using a configuration in which a laser diode to be used is selected from a plurality of laser diodes having output wavelengths different from each other. Further, the wavelength of the output light may be made variable by using a configuration in which a light emitting diode for outputting broadband light and a plurality of filters having transmission bands different from each other are used, and the filter to be used is switched.

The lens 12 is optically coupled to the light source 11. The lens 12 collimates the light output from the light source 11, and outputs the light to the polarizer 13.

The polarizer 13 is optically coupled to the lens 12. The polarizer 13 inputs the light collimated and output by the lens 12, and outputs linearly polarized light having a polarization plane (oscillation plane) according to an orientation of an optic axis of the polarizer 13 to the first prism 14.

The first prism 14 is optically coupled to the polarizer 13. The first prism 14 inputs the linearly polarized light output from the polarizer 13, and outputs two linearly polarized light beams orthogonal to each other in directions different from each other. A polarization plane of each of the two linearly polarized light beams orthogonal to each other and output from the first prism 14 is inclined by 45° with respect to the polarization plane of the linearly polarized light input from the polarizer 13 to the first prism 14.

The condenser lens 15 is optically coupled to the first prism 14. The condenser lens 15 focuses the two linearly polarized light beams orthogonal to each other output from the first prism 14 and irradiates the evaluation object S with the light beams. The two linearly polarized light beams orthogonal to each other output from the first prism 14 travel in the directions different from each other after being output from the first prism 14, and thus, focusing positions on the evaluation object S by the condenser lens 15 are slightly different.

The objective lens 21 inputs the two linearly polarized light beams orthogonal to each other and output from the evaluation object S in response to irradiation of the evaluation object S with the light by the irradiation optical system, collimates the light beams, and outputs the light beams to the second prism 22.

The second prism 22 is optically coupled to the objective lens 21. The second prism 22 inputs the two linearly polarized light beams orthogonal to each other and collimated and output by the objective lens 21, combines the light beams in the optical paths shifted by the first prism 14, and outputs the light to the lens 24.

Each of the first prism 14 and the second prism 22 may be a Wollaston prism or may be a Nomarski prism used in a normal differential interference contrast microscope.

The lenses 24, 31, and 34 provided on an optical path between the second prism 22 and the polarization camera 35 inputs the light output from the second prism 22, and form an image on the imaging plane of the polarization camera 35. The lens 24 inputs the light output from the second prism 22, and converges the light. The lens 31 inputs the light output from the lens 24 and reflected by the mirror 27, and collimates the light. The lens 34 inputs the light output from the lens 31 and reflected by the mirrors 36 and 37, and converges the light. The lens 31 and the lens 34 constitute a relay optical system.

The quarter wave plate 33 provided on an optical path between the lens 31 and the lens 34 inputs the light output from the second prism 22 and collimated through the lenses 24 and 31, and outputs two circularly polarized light beams having rotation directions different from each other.

The polarization camera 35 is optically coupled to the lens 34. The polarization camera 35 has the imaging plane disposed at a position where the image is formed by the imaging optical system. The polarization camera 35 inputs the two light beams circularly polarized in the rotation directions different from each other by the quarter wave plate 33, and acquires an interference image on the imaging plane for each of three or more polarization components.

As the polarization camera 35, for example, an image sensor (Polarsens (registered trademark)) commercialized by Sony Corporation, or an image sensor (Area Scan Polarization Sensor) or an image sensor (Line Scan Polarization Sensor) commercialized by Teledyne DALSA may be used.

The operation unit 39 is electrically connected to the polarization camera 35. The operation unit 39 generates a complex amplitude image (an amplitude image and a phase image) of the evaluation object S based on the interference images respectively for the three or more polarization components acquired by the polarization camera 35. The analysis unit 40 evaluates the evaluation object S based on the phase image acquired by the operation unit 39.

The operation unit 39 and the analysis unit 40 are units for performing the respective calculation processes of the refractive index distribution acquisition step S2 and the analysis step S3 according to a program, and are configured by, for example, a computer. The above units may be configured integrally.

The operation unit 39 and the analysis unit 40 include a processing unit including a CPU for performing various operational processing, a storage unit including a hard disk drive, a RAM, a ROM, and the like for storing data and the program, a display unit including a liquid crystal display for displaying processing results and the like, and an input unit including a keyboard, a mouse, and the like for receiving input of various conditions at the time of acquisition of the interference image and display of the image. The operation unit 39 and the analysis unit 40 may be constituted by a smart device such as a tablet terminal including a touch panel or the like as the input unit. Further, the operation unit and the storage unit of the operation unit 39 and the analysis unit 40 may be constituted by a field-programmable gate array (FPGA) or a microcomputer.

Figure 3:
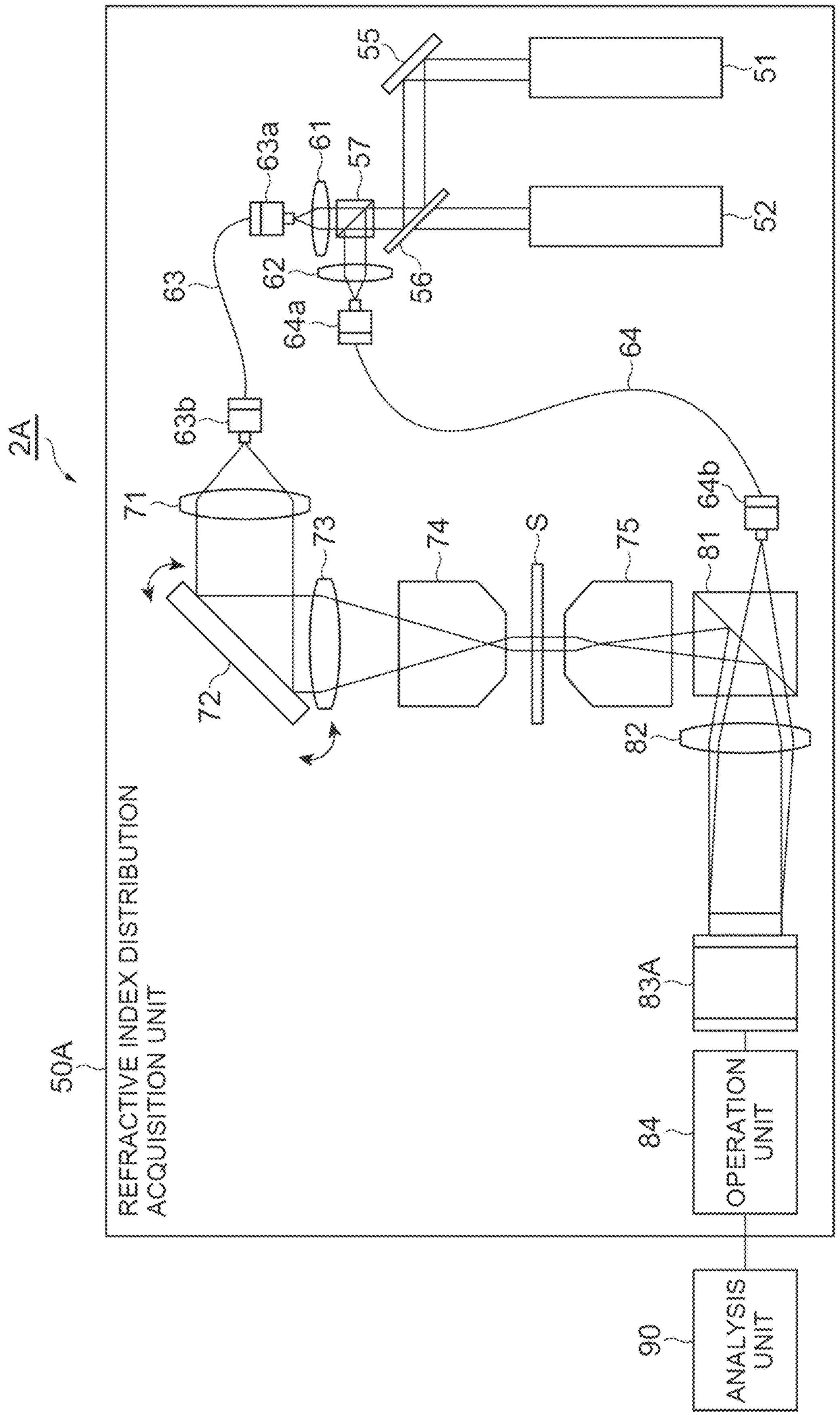
FIG. 3 is a diagram illustrating a configuration of a cell evaluation apparatus 2A.

FIG. 3 is a diagram illustrating a configuration of a cell evaluation apparatus 2A. The cell evaluation apparatus 2A includes a refractive index distribution acquisition unit 50A and an analysis unit 90. The refractive index distribution acquisition unit 50A performs the processing of the refractive index distribution acquisition step S2, and is configured based on the technique described in Non Patent Document 2. The analysis unit 90 performs the processing of the analysis step S3.

The refractive index distribution acquisition unit 50A includes laser light sources 51 and 52, a mirror 55, a dichroic mirror 56, a beam splitter 57, lenses 61 and 62, optical fibers

63 and 64, a lens 71, a mirror 72, a lens 73, a condenser lens 74, an objective lens 75, a beam splitter 81, a lens 82, a camera 83A, and an operation unit 84.

The laser light sources 51 and 52 output laser light beams having center wavelengths different from each other. The mirror 55 is optically coupled to the laser light source 51. The mirror 55 reflects the laser light output from the laser light source 51 to the dichroic mirror 56. The dichroic mirror 56 is optically coupled to the laser light source 52 and the mirror 55. The dichroic mirror 56 inputs the laser light output from the laser light source 52 and inputs the laser light arriving from the mirror 55, combines the input laser light beams, and outputs the laser light to the beam splitter 57.

The beam splitter 57 is optically coupled to the dichroic mirror 56. The beam splitter 57 inputs and splits the light arriving from the dichroic mirror 56, and outputs one split light to the lens 61 and outputs the other split light to the lens 62.

The lens 61 is optically coupled to the beam splitter 57. The lens 61 inputs the one split light arriving from the beam splitter 57, focuses the light on a light input end 63*a* of the optical fiber 63, and inputs the light to the light input end 63*a*. The optical fiber 63 guides the light input to the light input end 63*a* and outputs the light as diverging light from a light output end 63*b*.

The lens 62 is optically coupled to the beam splitter 57. The lens 62 inputs the other split light arriving from the beam splitter 57, focuses the light on a light input end 64*a* of the optical fiber 64, and inputs the light to the light input end 64*a*. The optical fiber 64 guides the light input to the light input end 64*a* and outputs the light as diverging light from a light output end 64*b*.

The lens 71 is optically coupled to the light output end 63*b* of the optical fiber 63, and collimates the light output as the diverging light from the light output end 63*b*. The mirror 72 is optically coupled to the lens 71, and reflects the light arriving from the lens 71 to the lens 73. An orientation of a reflection surface of the mirror 72 is changeable.

The lens 73 is optically coupled to the mirror 72. The condenser lens 74 is optically coupled to the lens 73. The lens 73 and the condenser lens 74 preferably constitute a 4*f* optical system. The lens 73 and the condenser lens 74 irradiate the evaluation object S with the light from a light irradiation direction according to the orientation of the reflection surface of the mirror 72.

The objective lens 75 is optically coupled to the condenser lens 74. The evaluation object S is disposed between the objective lens 75 and the condenser lens 74. The objective lens 75 inputs the light (object light) output from the condenser lens 74 and passed through the evaluation object S, and outputs the light to the beam splitter 81.

The beam splitter 81 is optically coupled to the objective lens 75, and further, is optically coupled to the light output end 64*b* of the optical fiber 64. The beam splitter 81 inputs the light (object light) output and arriving from the objective lens 75 and inputs the light (reference light) output and arriving from the light output end 64*b*, and outputs the light to the lens 82. The lens 82 is optically coupled to the beam splitter 81, collimates the object light and the reference light respectively arriving from the beam splitter 81, and outputs the light to the camera 83A.

The camera 83A is a color camera, and is optically coupled to the lens 82. The camera 83A images an interference fringe image (interference intensity image) generated by interference between the object light and the reference light arriving from the lens 82. An incident direction of the reference light is inclined with respect to an incident direction of the object light on an imaging plane of the camera 83A. A position at which the object light and the reference light are combined by the beam splitter 81 may be a position in the subsequent stage of the imaging lens, and in addition, in consideration of the influence of aberration, it is desirable that the position is set between the objective lens 75 and the lens 82 as illustrated in the diagram.

The operation unit 84 is electrically connected to the camera 83A. The operation unit 84 analyzes the interference image (color image) acquired by the camera 83A, and generates the interference images at the respective output wavelengths of the laser light sources 51 and 52. In addition, the operation unit 84 calculates a three-dimensional refractive index distribution of the evaluation object S at each wavelength by processing the interference images acquired by variously setting the light incident direction on the evaluation object S by the change of the orientation of the reflection surface of the mirror 72.

The analysis unit 90 evaluates the evaluation object S based on the refractive index distribution image acquired by the operation unit 84. The operation unit 84 and the analysis unit 90 are also units for performing the respective calculation processes of the refractive index distribution acquisition step S2 and the analysis step S3, and are configured by, for example, a computer. The above units may be configured integrally.

Figure 4:
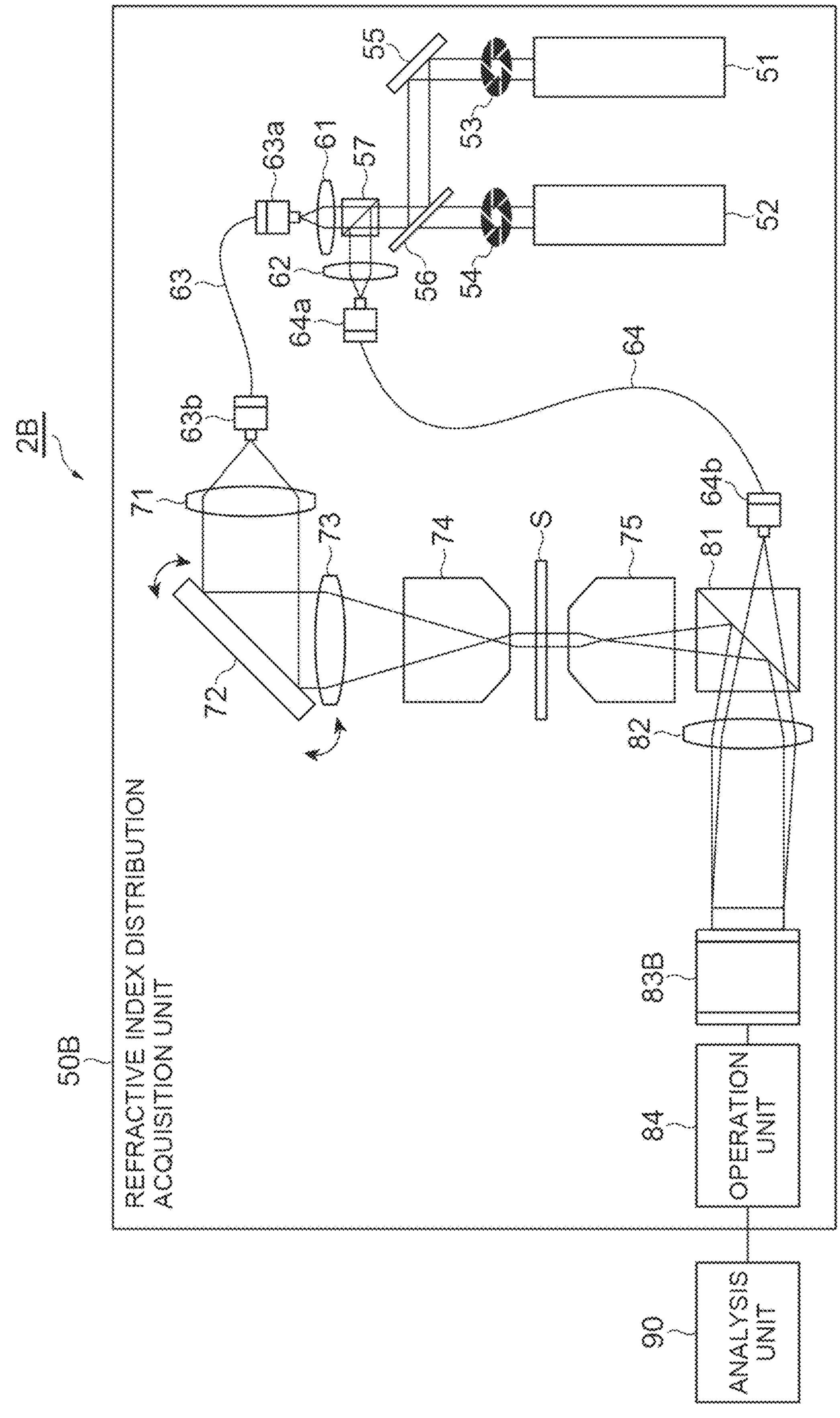
FIG. 4 is a diagram illustrating a configuration of a cell evaluation apparatus 2B.

FIG. 4 is a diagram illustrating a configuration of a cell evaluation apparatus 2B. The cell evaluation apparatus 2B includes a refractive index distribution acquisition unit 50B and the analysis unit 90. Compared with the refractive index distribution acquisition unit 50A (FIG. 3), the refractive index distribution acquisition unit 50B (FIG. 4) is different in that shutters 53 and 54 are further provided, and a monochrome camera 83B is provided instead of the color camera 83A.

The shutter 53 is provided on an optical path between the laser light source 51 and the mirror 55, and allows or blocks propagation of the laser light from the laser light source 51 to the mirror 55. The shutter 54 is provided on an optical path between the laser light source 52 and the dichroic mirror 56, and allows or blocks propagation of the laser light from the laser light source 52 to the dichroic mirror 56. The shutter 53 and the shutter 54 do not allow the propagation of the laser light at the same time. The camera 83B separately images the interference image at the output wavelength of the laser light source 51 and the interference image at the output wavelength of the laser light source 52.

The processing of the refractive index distribution acquisition step S2 of the cell evaluation method according to the present embodiment can be performed by using each of the refractive index distribution acquisition units 10, 50A, and 50B of the above cell evaluation apparatuses, and in addition, it is not limited to the configurations described above, and may be performed by using another configuration capable of acquiring the phase image or the refractive index distribution image of the evaluation object S.

Next, each of the labeling step S1, the refractive index distribution acquisition step S2, and the analysis step S3 of the cell evaluation method will be described in more detail.

In general, it is known that the longer the wavelength of the light, the lower the refractive index of the substance. For example, it is described in Non Patent Document 3 that, for each of protein and DNA, the refractive index at a wavelength of 400 nm is lower compared with the refractive index at a wavelength of 310 nm. Further, in an unlabeled portion, the longer the wavelength of the light, the lower the refractive index of the entire unlabeled portion. Therefore, it is not easy to observe the specific component in the cell in the case in which the labeling (labeling indicating a larger change of the refractive index than a change of the refractive index in the unlabeled component) is not performed.

In the labeling step S1, as the labeling substance for labeling the specific component in the cell being the evaluation object, the labeling substance having the refractive indices different from each other respectively at the first wavelength and the second wavelength, which are the wavelengths of the light used in the subsequent refractive index distribution acquisition step S2, is used. The specific component may be a specific molecule or a specific structure, and for example, may be a vesicle structure, a nucleolus, a mitochondrion, a specific protein, or the like, or may be a whole cell.

The labeling substance for labeling the specific component in the labeling step S1 may be a labeling substance having a higher refractive index at a longer wavelength out of the first wavelength and the second wavelength than a refractive index at a shorter wavelength, and further, may be a labeling substance having a lower refractive index at the longer wavelength than a refractive index at the shorter wavelength.

Further, the labeling substance for labeling the specific component in the labeling step S1 is preferably a light absorbing labeling substance having an absorption peak at a predetermined wavelength $\lambda_0$. In this case, in the refractive index distribution acquisition step S2, it is preferable to acquire the refractive index distribution of the cell at each of the first wavelength $\lambda_1$ and the second wavelength $\lambda_2$ set on a short wavelength side or a long wavelength side with respect to the predetermined wavelength $\lambda_0$. Further, in the refractive index distribution acquisition step S2, it is also preferable to acquire the refractive index distribution of the cell at each of the first wavelength $\lambda_1$ and the second wavelength $\lambda_2$, with one wavelength out of the first wavelength $\lambda_1$ and the second wavelength $\lambda_2$ set on the short wavelength side with respect to the predetermined wavelength $\lambda_0$, and the other wavelength set on the long wavelength side with respect to the predetermined wavelength $\lambda_0$.

FIG. 5 includes diagrams schematically showing a light absorption spectrum and a refractive index spectrum of the light absorbing labeling substance. (a) in FIG. 5 shows the light absorption spectrum. (b) in FIG. 5 shows the refractive index spectrum. As shown in these diagrams, the light absorbing labeling substance has the absorption peak at the predetermined wavelength $\lambda_0$, and the refractive index has a local minimum on the short wavelength side with respect to the predetermined wavelength $\lambda_0$, and further, the refractive index has a local maximum on the long wavelength side with respect to the predetermined wavelength $\lambda_0$. In general, the relationship between the light absorption spectrum and the refractive index spectrum is represented by the Kramers-Kronig relations (see Non Patent Document 4).

Therefore, in the case in which the light absorbing labeling substance having the absorption peak at the predetermined wavelength $\lambda_0$ is used, as shown in (b) in FIG. 5, the first wavelength $\lambda_1$ can be set near the wavelength at which the refractive index has the local minimum on the short wavelength side with respect to the predetermined wavelength $\lambda_0$, and the second wavelength $\lambda_2$ can be set near the wavelength at which the refractive index has the local maximum on the long wavelength side with respect to the predetermined wavelength $\lambda_0$.

Figure 6:
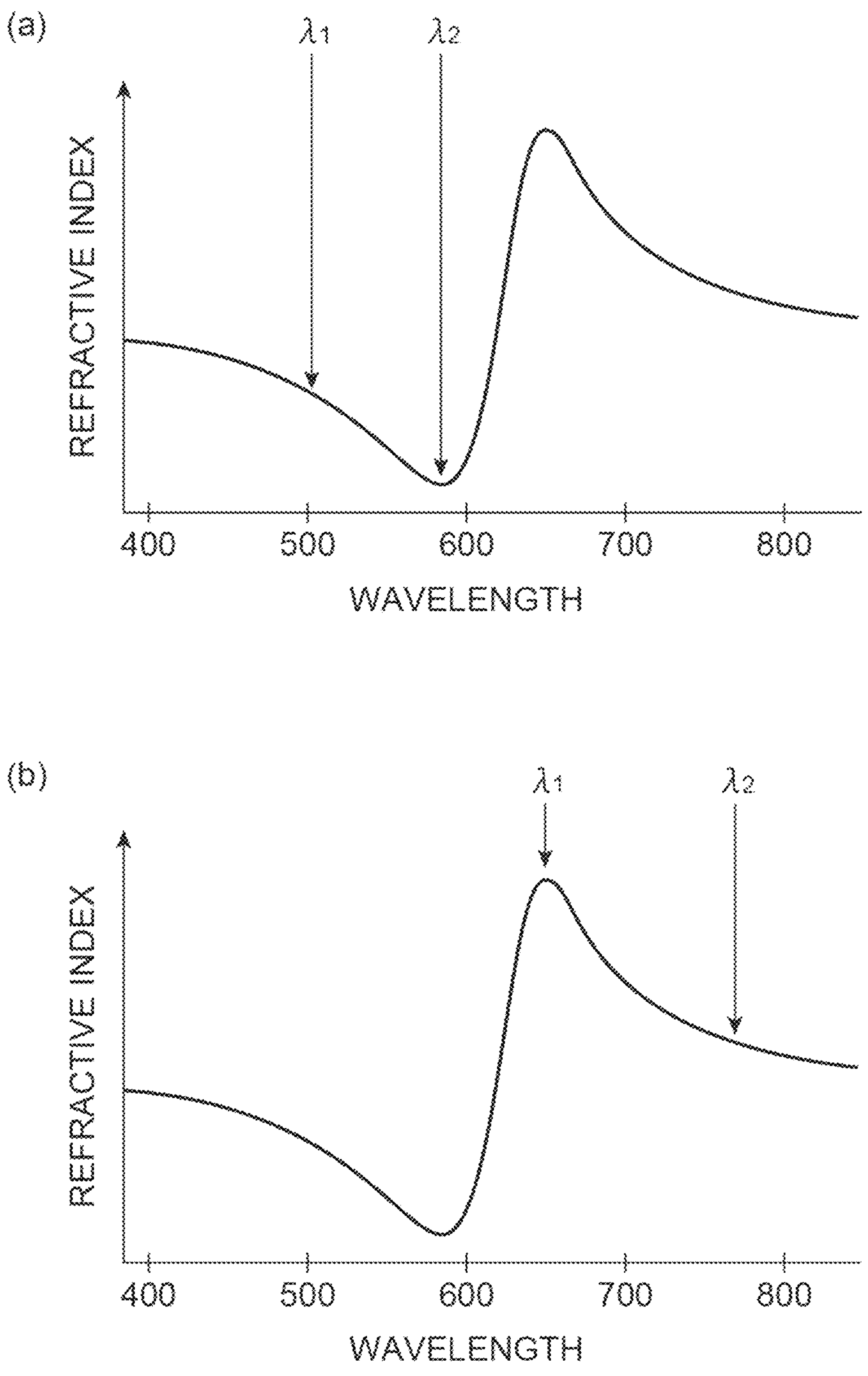
FIG. 6 includes (a), (b) diagrams schematically showing the refractive index spectra of the light absorbing labeling substance.

As shown in the refractive index spectrum of the light absorbing labeling substance in (a) in FIG. 6, there is a wavelength range in which the wavelength dependency of the refractive index is large on the short wavelength side from the vicinity of the wavelength at which the refractive index has the local minimum, and in this case, the first wavelength $\lambda_1$ and the second wavelength $\lambda_2$ may be set in the above wavelength range. Further, as shown in the refractive index spectrum of the light absorbing labeling substance in (b) in FIG. 6, there is also a wavelength range in which the wavelength dependency of the refractive index is large on the long wavelength side from the vicinity of the wavelength at which the refractive index has the local maximum, and in this case, the first wavelength $\lambda_1$ and the second wavelength $\lambda_2$ may be set in the above wavelength range.

As described above, the first wavelength $\lambda_1$ and the second wavelength $\lambda_2$ are respectively set, and in the refractive index distribution acquisition step S2, the refractive index distribution of the cell in which the specific component is labeled with the light absorbing labeling substance is acquired at each of the first wavelength $\lambda_1$ and the second wavelength $\lambda_2$.

Examples of the light absorbing labeling substance capable of labeling the specific component in the living cell include brilliant cresyl blue, new methylene blue, neutral red, janus green B, nile blue, bismarck brown, nile red, oil red, and the like. Examples of the light absorbing labeling substance capable of labeling the specific component in the dead cell include trypan blue, and the like.

Further, examples of the light absorbing labeling substance capable of labeling the specific component in the cell include, although a fixation process for the cell is required, hematoxylin, eosin, picric acid, orange G, azocarmine G, fuchsine, aniline blue, azure blue, azure II, sudan III, sudan black, resorcin, kernechtrot, and the like.

As an example of the light absorbing labeling substance capable of labeling the specific component in the cell, a natural chromoprotein can also be used. Examples of the above natural chromoprotein include blue protein (cjBlue) derived from sea anemone (*Cnidopus japonicus*), blue protein (rpulFKz1) derived from jellyfish (*Rhizostoma pulmo*), purple protein (gfasCP) derived from coral (*Galaxea fascicularis*), pink protein (asFP595) derived from sea anemone (*Anemonia sulcata*), blue protein (Rtms5) derived from coral (*Montipora efflorescens*), blue protein (aeCP597) derived from sea anemone (*Actinia equina*), and the like. An artificial chromoprotein obtained by modifying the natural chromoprotein may also be used.

Further, as the chromoprotein, a fluorescent chromoprotein may also be used. Examples of the above fluorescent chromoprotein include red fluorescent protein (eforRed) derived from coral (*Echinopora forskaliana*), and the like.

The labeling substance for labeling the specific component in the cell may be a construct for intracellular expression in which a DNA sequence encoding a chromoprotein V (light absorbing polypeptide) is connected to a N-terminus or a C-terminus of a DNA sequence encoding an arbitrary protein W. The construct for intracellular expression may be designed to be expressed under control of a cytomegalovirus (CMV) promoter or the like. In the labeling step S1, the construct for intracellular expression described above is introduced into the cell by a lipofection method, an electroporation method, or the like to label the specific component in the cell. By the above introduction, an artificial fusion protein is expressed.

A plurality of types of the labeling substances may be used at the same time. That is, in the labeling step S1, another specific component in the cell may be labeled with another labeling substance having refractive indices different from each other respectively at a third wavelength and a fourth wavelength. In this case, in the refractive index distribution acquisition step S2, the refractive index distribution of the cell labeled in the labeling step S1 is acquired at each of the first wavelength and the second wavelength, and in addition, is also acquired at each of the third wavelength and the fourth wavelength.

In the analysis step S3, the distribution of the other specific component in the cell is also evaluated by comparing the refractive index distributions respectively at the third wavelength and the fourth wavelength. The first wavelength or the second wavelength may be equal to the third wavelength or the fourth wavelength. In the case in which the two types of the labeling substances are used at the same time, the number of the wavelengths of the light used in the refractive index distribution acquisition step S2 may be four, may be three, or may be two.

The first wavelength and the second wavelength can be determined, for example, as follows. In the case in which the light absorption spectrum of the light absorbing labeling substance is known, the refractive index spectrum may be estimated from the light absorption spectrum based on the Kramers-Kronig relations, and the first wavelength and the second wavelength may be set near the local minimum value and near the local maximum value in the refractive index profile.

In the case in which the light absorption spectrum of the light absorbing labeling substance is unknown, after measuring the light absorption spectrum, the refractive index spectrum may be estimated from the light absorption spectrum based on the Kramers-Kronig relations, and the first wavelength and the second wavelength may be set near the local minimum value and near the local maximum value in the refractive index profile.

After the first wavelength and the second wavelength are set, the processing of the refractive index distribution acquisition step S2 may be performed for the first wavelength and the second wavelength which are set as described above. Further, after the refractive index distribution is acquired for each of several wavelengths in the refractive index distribution acquisition step S2, the first wavelength and the second wavelength at which a difference of the refractive index distributions is observed may be set out of the above wavelengths.

In the case in which the first wavelength and the second wavelength can be set freely, the first wavelength and the second wavelength may be set to the local minimum value and the local maximum value in the refractive index profile. In the case in which the first wavelength and the second wavelength are selected from several fixed wavelengths, two wavelengths having the largest refractive index difference out of the fixed wavelengths may be set as the first wavelength and the second wavelength. Further, the refractive index distribution may be always acquired for one wavelength out of the first wavelength and the second wavelength, and for the other wavelength, the refractive index distribution may be acquired at the wavelength set based on a color of the light absorbing labeling substance.

Figure 7:
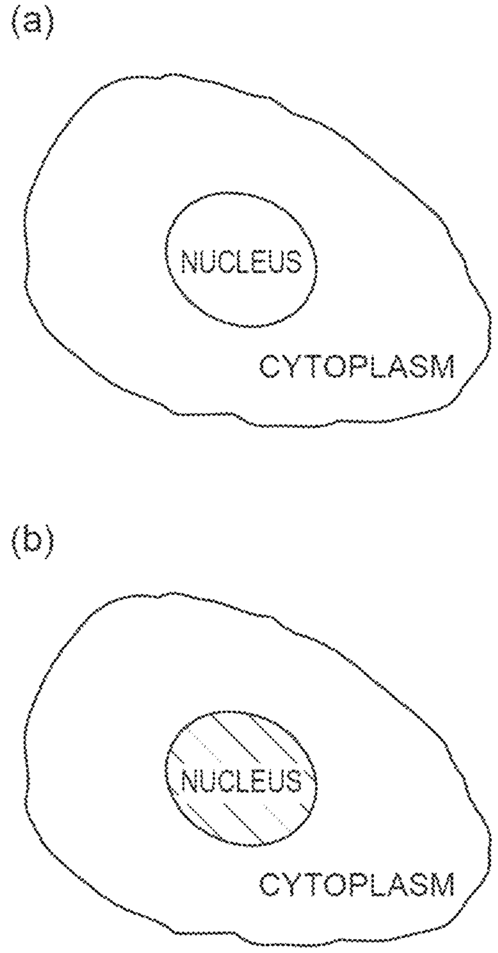
FIG. 7 includes diagrams schematically showing refractive index distributions of a cell in which a cell nucleus as a specific component is labeled with the light absorbing labeling substance, and shows (a) the refractive index distribution of the cell at a first wavelength $\lambda_1$, and (b) the refractive index distribution of the cell at a second wavelength $\alpha_2$.

In the analysis step S3, the distribution of the specific component in the cell is evaluated by comparing the refractive index distributions respectively at the first wavelength $\lambda_1$ and the second wavelength $\lambda_2$. FIG. 7 includes diagrams schematically showing the refractive index distributions of the cell in which a cell nucleus as the specific component is labeled with the labeling substance. (a) in FIG. 7 shows the refractive index distribution of the cell at the first wavelength $\lambda_1$. (b) in FIG. 7 shows the refractive index distribution of the cell at the second wavelength $\lambda_2$.

As compared with the refractive index distribution of the cell at the first wavelength $\lambda_1$ ((a) in FIG. 7), in the refractive index distribution of the cell at the second wavelength $\lambda_2$ ((b) in FIG. 7), the refractive index in a region of the cell nucleus labeled with the labeling substance (a hatched region in (b) in FIG. 7) can be increased. By comparing the refractive index distribution of the cell at the first wavelength $\lambda_1$ ((a) in FIG. 7) and the refractive index distribution of the cell at the second wavelength $\lambda_2$ ((b) in FIG. 7), it is possible to evaluate a position, a shape, a size, and the like of the cell nucleus in the cell. As described above, in the analysis step S3, the distribution of the specific component in the cell can be evaluated by comparing the refractive index distributions respectively at the first wavelength $\lambda_1$ and the second wavelength $\lambda_2$.

In the analysis step S3, the distribution of the specific component in the cell may be evaluated based on a difference between the refractive index distributions of the cell respectively at the first wavelength $\lambda_1$ and the second wavelength $\lambda_2$. Further, the distribution of the specific component in the cell may be evaluated based on a ratio between these two refractive index distributions. In the case in which the refractive index distribution image is generated after the phase image of the cell is acquired, the difference or the ratio between the two refractive index distributions may be obtained after performing correction based on the difference of the wavelengths, or the ratio between the two refractive index distributions may be obtained without performing the correction based on the difference of the wavelengths.

It is also preferable that the analysis of the specific component in the cell is performed by superimposing a comparison result of the refractive index distributions respectively at the first wavelength $\lambda_1$ and the second wavelength $\lambda_2$ on an intensity image or a fluorescence image of the cell. Hereinafter, an image representing the difference or the ratio between the refractive index distribution images of the cell respectively at the first wavelength $\lambda_1$ and the second wavelength $\lambda_2$ is referred to as a "refractive index variation image".

In the analysis step S3, various analyses can be performed with respect to the specific component in the cell by using the refractive index distribution image (and further using other images).

FIG. 8 includes diagrams for describing a first analysis example in the analysis step S3. (a) in FIG. 8 is a diagram schematically showing the refractive index distribution image. (b) in FIG. 8 is a diagram schematically showing the refractive index variation image. (c) in FIG. 8 is a diagram in which the refractive index distribution image ((a) in FIG. 8) and the refractive index variation image ((b) in FIG. 8) are superimposed. These diagrams show the example in which a specific vesicle structure out of vesicle structures and cell structures in the cell is labeled with the labeling substance.

In the refractive index distribution image ((a) in FIG. 8), it is not possible to distinguish between the labeled specific vesicle structure and the unlabeled vesicle structures and other cell structures in the cell. On the other hand, in the refractive index variation image ((b) in FIG. 8), it is possible to distinguish between the labeled specific vesicle structure and the unlabeled vesicle structures and other cell structures in the cell.

Therefore, by comparing the refractive index distribution image ((a) in FIG. 8) and the refractive index variation image ((b) in FIG. 8), or by superimposing and displaying the refractive index distribution image ((a) in FIG. 8) and the refractive index variation image ((b) in FIG. 8), the distribution of the vesicle structures and the other cell structures in the cell can be obtained, and further, the distribution of the labeled specific vesicle structure can also be obtained.

In the first analysis example, the average refractive index and the like of the labeled specific vesicle structure can be analyzed, and further, the specific vesicle structure can be evaluated based on the above value. For example, substances contained in the vesicle can be estimated, and a vacuole and a secretory vesicle can be identified.

In the case in which a localization property of the labeling substance is unknown, and an approximate structure in the cell can be identified from the refractive index distribution image, it is possible to evaluate a position at which the labeling substance is localized, and for example, the localization property of the specific vesicle structure in the cell (such as a tendency of the localization around the cell nucleus) can be observed. In the case in which the localization property of the labeling substance is known, and it is difficult to identify the structure in the cell from the refractive index distribution image, segmentation of the refractive index distribution image can be performed, and for example, it is possible to evaluate the feature of the refractive index for discriminating the specific vesicle structure.

In addition, the wavelength of the light used at the time of the acquisition of the refractive index distribution image may be equal to or may be different from any wavelength of the light used at the time of the acquisition of the refractive index variation image. For example, in the case in which the refractive indices are to be compared between the labeled component and the unlabeled component, the wavelength of the light used at the time of the acquisition of the refractive index distribution image may be set to a wavelength which is not in a wavelength region in which the refractive index spectrum of the labeling substance greatly changes.

Figure 9:
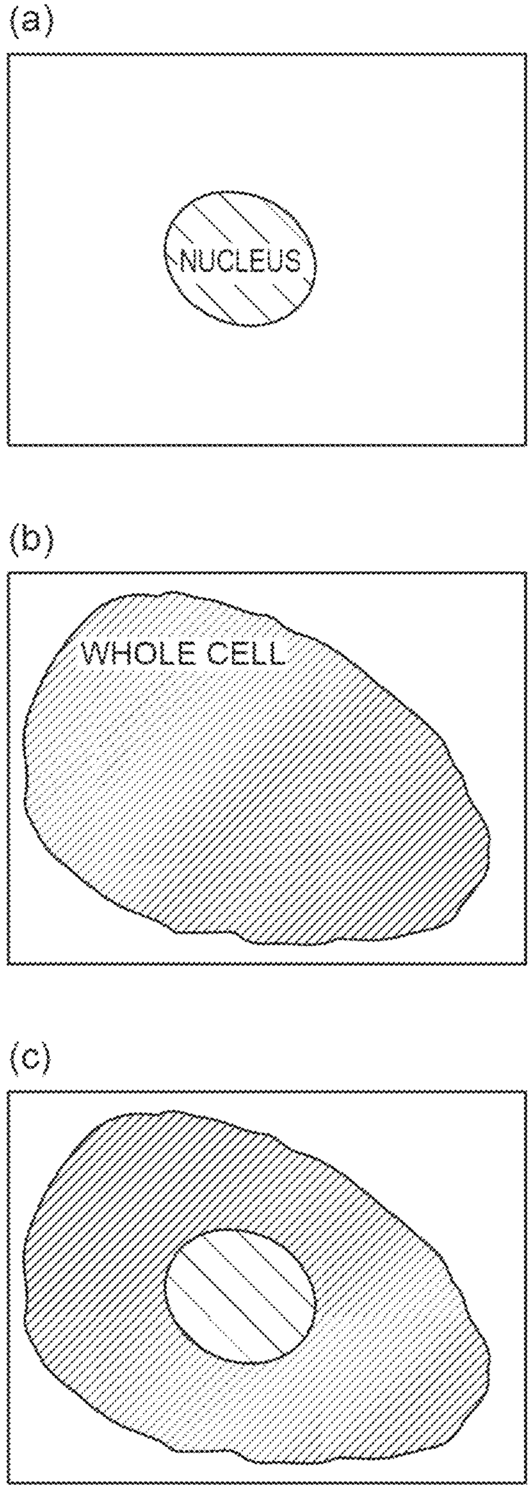
FIG. 9 includes diagrams describing a second analysis example in the analysis step S3, and shows (a) a diagram schematically showing the refractive index variation image acquired by labeling the cell nucleus with the labeling substance, (b) a diagram schematically showing the refractive index variation image acquired by labeling a whole cell with the labeling substance, and (c) a diagram in which the refractive index variation image ((a) in FIG. 9) and the refractive index variation image ((b) in FIG. 9) are superimposed.

FIG. 9 includes diagrams for describing a second analysis example in the analysis step S3. (a) in FIG. 9 is a diagram schematically showing the refractive index variation image acquired by labeling the cell nucleus with the labeling substance. (b) in FIG. 9 is a diagram schematically showing the refractive index variation image acquired by labeling the whole cell with the labeling substance. (c) in FIG. 9 is a diagram in which the refractive index variation image ((a) in FIG. 9) and the refractive index variation image ((b) in FIG. 9) are superimposed.

In the second analysis example, a ratio of the cell nucleus/a cytoplasm can be analyzed by obtaining an area of the cell nucleus based on the refractive index variation image ((a) in FIG. 9), obtaining an area of the whole cell based on the refractive index variation image ((b) in FIG. 9), and obtaining a ratio of the above areas. Further, a region other than the cell nucleus in the whole cell can be identified as the cytoplasm, and further, a position of the cell nucleus in the whole cell can also be identified. It is also possible to estimate the number of cells contained in a cell mass by labeling the cells only with the labeling substance of the cell nucleus and counting the number of cell nuclei.

Figure 10:
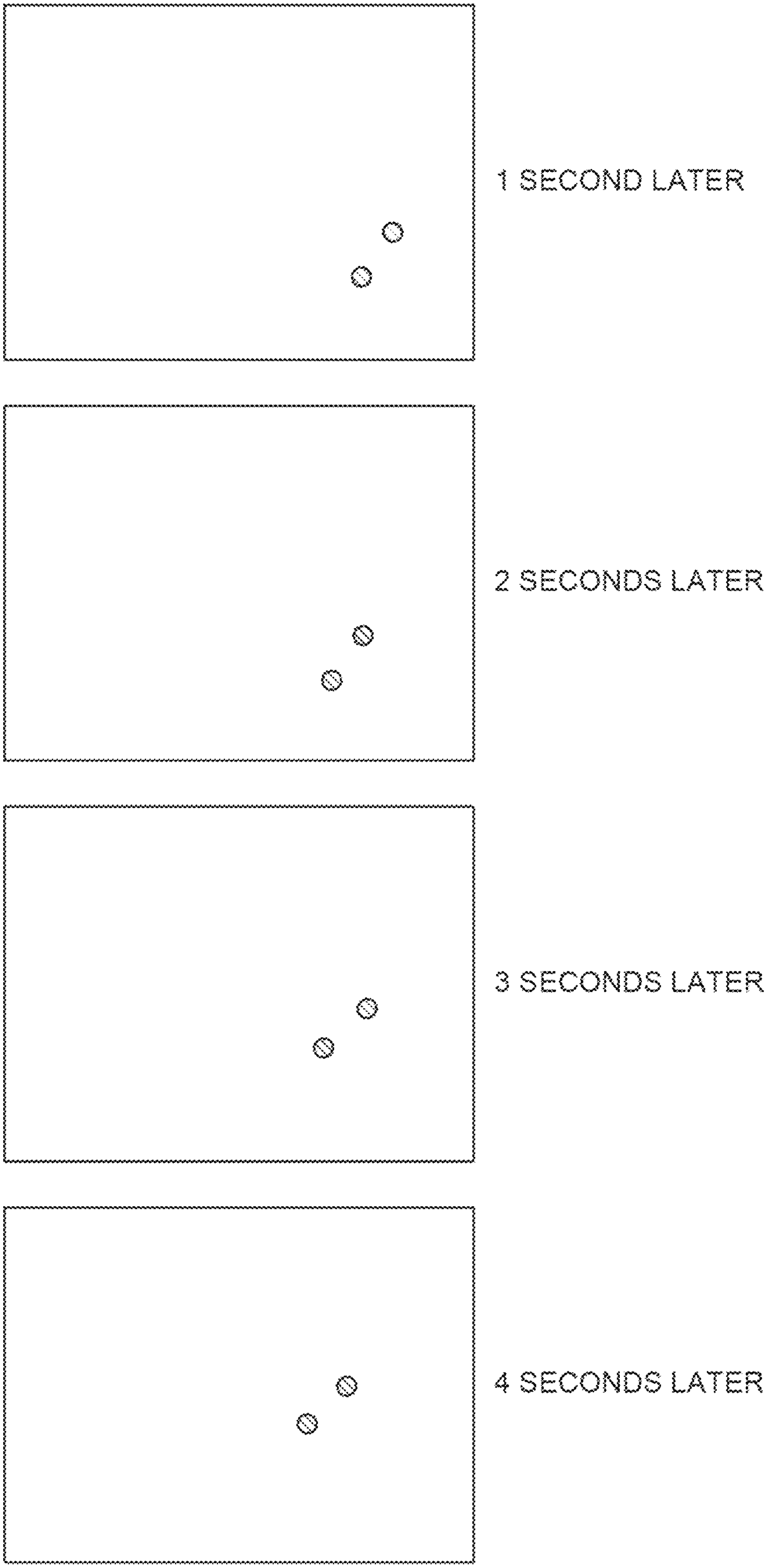
FIG. 10 is a diagram describing a third analysis example in the analysis step S3, and schematically shows a plurality of refractive index variation images acquired at a predetermined time interval.
Figure 11:
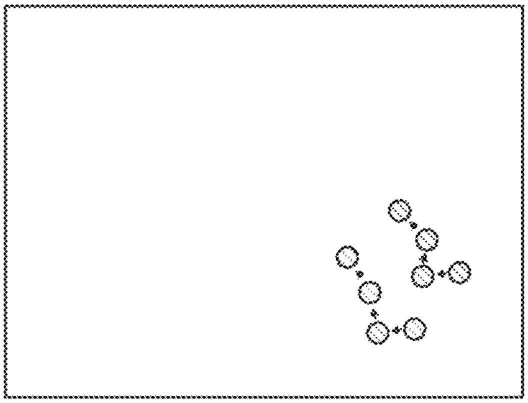
FIG. 11 is a diagram describing the third analysis example in the analysis step S3, and shows a diagram in which the plurality of refractive index variation images (FIG. 10) acquired at the predetermined time interval are superimposed.
Figure 12:
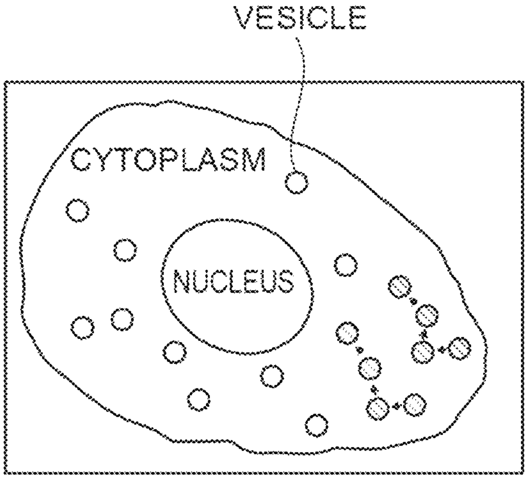
FIG. 12 is a diagram describing the third analysis example in the analysis step S3, and shows a diagram in which the plurality of refractive index variation images (FIG. 10) acquired at the predetermined time interval and the refractive index distribution image are superimposed.

FIG. 10 to FIG. 12 are diagrams for describing a third analysis example in the analysis step S3. FIG. 10 is a diagram schematically showing a plurality of refractive index variation images acquired at a predetermined time interval. FIG. 11 is a diagram in which the plurality of refractive index variation images (FIG. 10) acquired at the predetermined time interval are superimposed. FIG. 12 is a diagram in which the plurality of refractive index variation images (FIG. 10) acquired at the predetermined time interval and the refractive index distribution image are superimposed.

In the third analysis example, it is possible to analyze a state of change with time of a position of the specific component labeled with the labeling substance in the cell. In the case in which the fluorescence image is acquired, it is necessary to perform irradiation with excitation light with high power, and thus there are problems of phototoxicity and photobleaching, and on the other hand, in the present embodiment, it is not necessary to perform irradiation with light with high power, and thus problems of the phototoxicity and the photobleaching are minimized, and time lapse observation of the cell for a long time can be performed.

Figure 13:
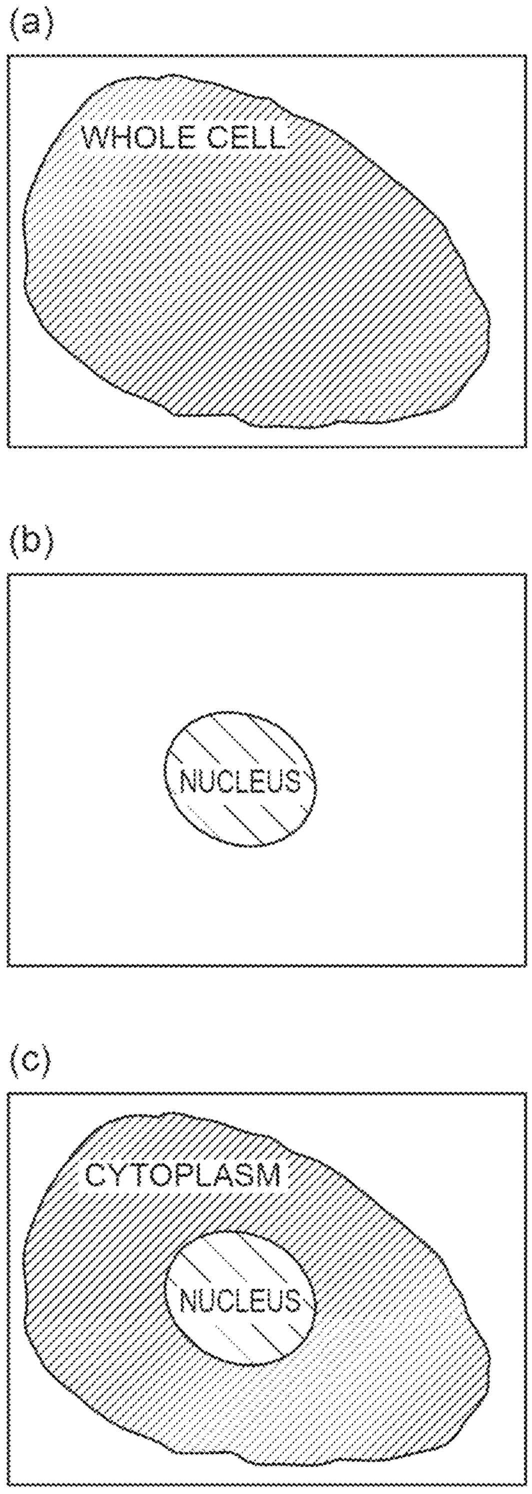
FIG. 13 includes diagrams describing a fourth analysis example in the analysis step S3, and shows (a) a diagram schematically showing a fluorescence image or an intensity image of the whole cell, (b) a diagram schematically showing the refractive index variation image acquired by labeling the cell nucleus with the labeling substance, and (c) a diagram in which the fluorescence image or the intensity image of the whole cell ((a) in FIG. 13) and the refractive index variation image ((b) in FIG. 13) are superimposed.

FIG. 13 includes diagrams for describing a fourth analysis example in the analysis step S3. (a) in FIG. 13 is a diagram schematically showing the fluorescence image or the intensity image of the whole cell. (b) in FIG. 13 is a diagram schematically showing the refractive index variation image acquired by labeling the cell nucleus with the labeling substance. (c) in FIG. 13 is a diagram in which the fluorescence image or the intensity image of the whole cell ((a) in FIG. 13) and the refractive index variation image ((b) in FIG. 13) are superimposed.

In the fourth analysis example, the ratio of the cell nucleus/the cytoplasm can be analyzed by obtaining the area of the whole cell based on the fluorescence image or the intensity image of the whole cell ((a) in FIG. 13), obtaining the area of the cell nucleus based on the refractive index variation image ((b) in FIG. 13), and obtaining the ratio of the above areas. Further, the region other than the cell nucleus in the whole cell can be identified as the cytoplasm, and further, the position of the cell nucleus in the whole cell can also be identified.

FIG. 14 includes diagrams for describing a fifth analysis example in the analysis step S3. (a) in FIG. 14 is a diagram schematically showing the fluorescence image or the intensity image of the cell nucleus. (b) in FIG. 14 is a diagram schematically showing the refractive index variation image acquired by labeling by using the labeling substance for an unknown labeling object. (c) in FIG. 14 is a diagram in which the fluorescence image or the intensity image of the cell nucleus ((a) in FIG. 14) and the refractive index variation image ((b) in FIG. 14) are superimposed.

In the fifth analysis example, in the case in which the fluorescence image or the intensity image of the cell nucleus ((a) in FIG. 14) and the refractive index variation image ((b) in FIG. 14) coincide with each other, it can be evaluated that the labeling substance for the unknown labeling object is a labeling substance which can label the cell nucleus. Further, by comparing the fluorescence image or the intensity image of the cell nucleus ((a) in FIG. 14) and the refractive index variation image ((b) in FIG. 14), it is also possible to perform correction at the time of the generation of the refractive index variation image based on the refractive index distribution image.

In addition, the wavelength of the light used at the time of the acquisition of the fluorescence image or the intensity image may be equal to or may be different from any wavelength of the light used at the time of the acquisition of the refractive index variation image.

In the case in which the two types of the labeling substances are used, in the analysis step S3, various analyses can be further performed with respect to the two types of the specific components in the cell by using the two refractive index distribution images (and further using other images).

Figure 15:
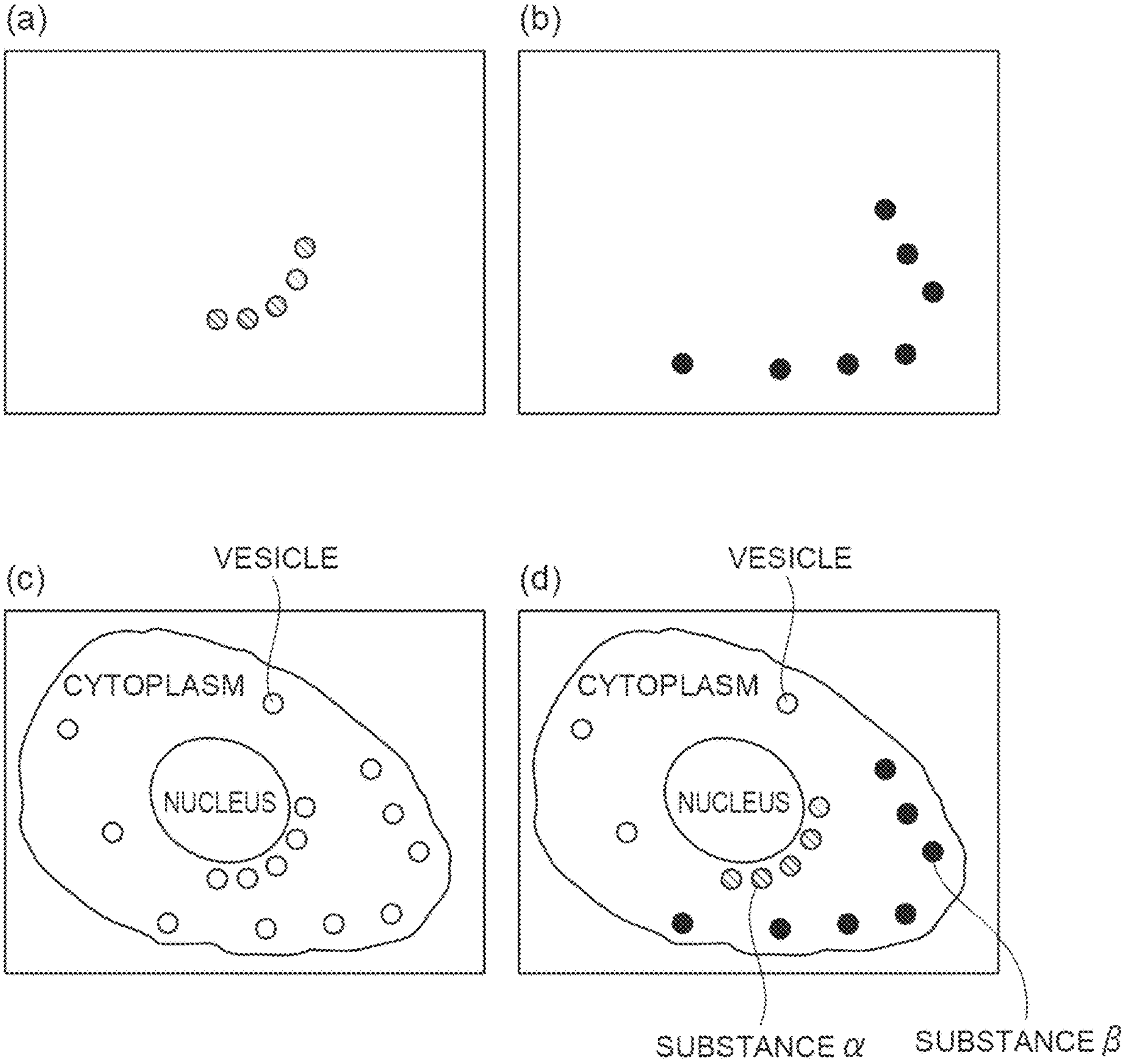
FIG. 15 includes diagrams describing a sixth analysis example in the analysis step S3, and shows (a) a diagram schematically showing the refractive index variation image acquired by labeling a specific vesicle with a labeling substance α, (b) a diagram schematically showing the refractive index variation image acquired by labeling another specific vesicle with a labeling substance β, (c) a diagram schematically showing the refractive index distribution image, and (d) a diagram in which the refractive index variation image ((a) in FIG. 15), the refractive index variation image ((b) in FIG. 15), and the refractive index distribution image ((c) in FIG. 15) are superimposed.

FIG. 15 includes diagrams for describing a sixth analysis example in the analysis step S3. (a) in FIG. 15 is a diagram schematically showing the refractive index variation image acquired by labeling a specific vesicle with a labeling substance α. (b) in FIG. 15 is a diagram schematically showing the refractive index variation image acquired by labeling another specific vesicle with a labeling substance β. (c) in FIG. 15 is a diagram schematically showing the refractive index distribution image. (d) in FIG. 15 is a diagram in which the refractive index variation image ((a) in FIG. 15), the refractive index variation image ((b) in FIG. 15), and the refractive index distribution image ((c) in FIG. 15) are superimposed.

In the sixth analysis example, it is possible to know that a region in which the specific vesicles labeled with the labeling substance α are present and a region in which the other specific vesicles labeled with the labeling substance β are present are different from each other, and for example, it is possible to know that the former vesicles are present in a region close to the cell nucleus and the latter vesicles are present in a region far from the cell nucleus.

The distribution of the specific component can be evaluated not only for the single cell but also for the cell mass in which a plurality of cells are three-dimensionally aggregated.

Figure 16:
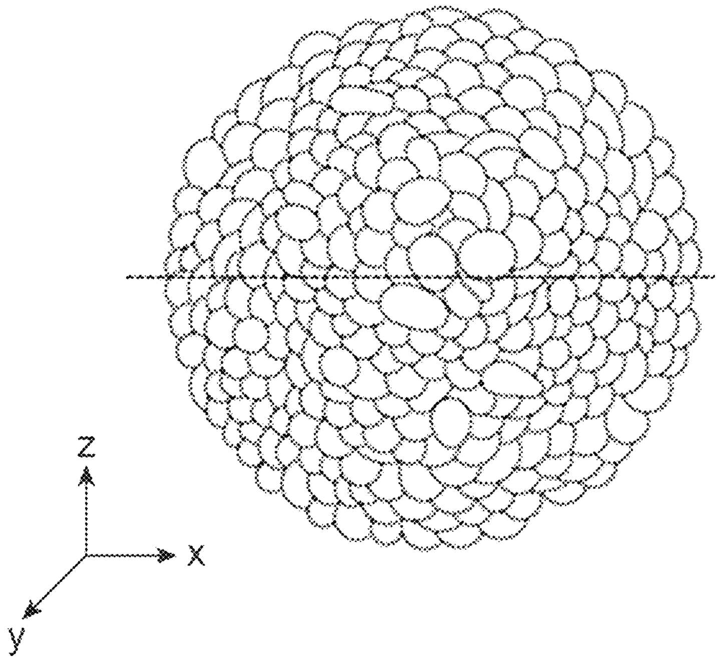
FIG. 16 is a diagram schematically showing a cell mass.

FIG. 16 is a diagram schematically showing the cell mass. The phase image or the refractive index distribution image in an arbitrary cross section (a cross section indicated by a dashed line in the diagram) of the cell mass can be obtained, and the refractive index variation image in the cross section can be acquired from the above image. Not only the cross section of the cell mass but also a tomographic image or a three-dimensional refractive index distribution image can also be obtained.

FIG. 17 includes diagrams for describing a seventh analysis example in the analysis step S3. (a) in FIG. 17 is a diagram schematically showing the refractive index variation image acquired by labeling the specific component in each of the cells included in the cell mass with the labeling substance α. (b) in FIG. 17 is a diagram schematically showing the refractive index distribution image. (c) in FIG. 17 is a diagram in which the refractive index variation image ((a) in FIG. 17) and the refractive index distribution image ((b) in FIG. 17) are superimposed.

In the seventh analysis example, it is possible to know a region in which the cells each including the specific component labeled with the labeling substance α are present in the cell mass, and for example, it is possible to know that the above cells are present in a peripheral region.

It is also possible to evaluate the distributions of the two types of the specific components in the cell mass by using the two types of the labeling substances.

Figure 18:
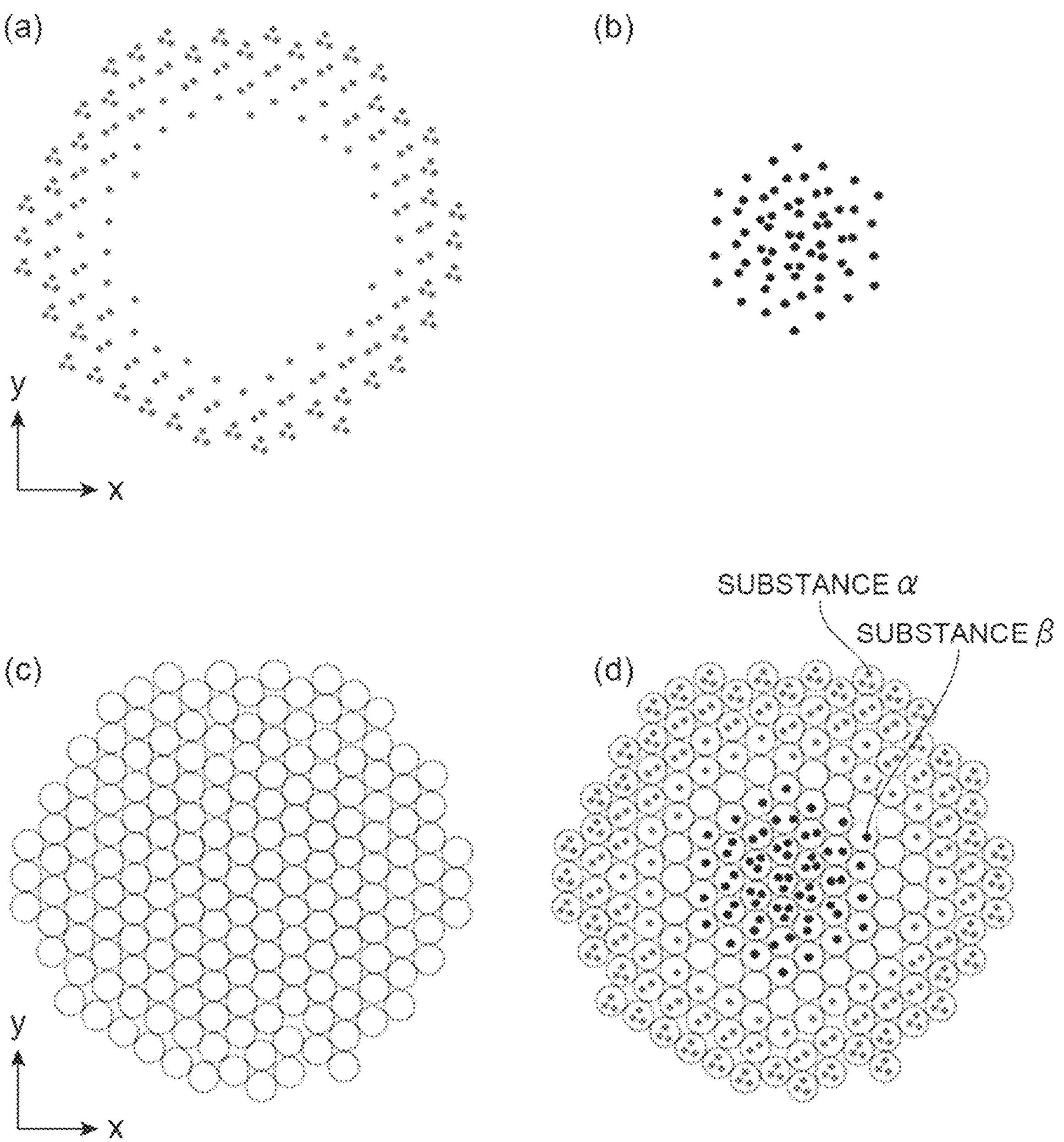
FIG. 18 includes diagrams describing an eighth analysis example in the analysis step S3, and shows (a) a diagram schematically showing the refractive index variation image acquired by labeling the specific component in each of the cells included in the cell mass with the labeling substance α, (b) a diagram schematically showing the refractive index variation image acquired by labeling the other specific component in each of the cells included in the cell mass with the other labeling substance β, (c) a diagram schematically showing the refractive index distribution image, and (d) a diagram in which the refractive index variation image ((a) in FIG. 18), the refractive index variation image ((b) in FIG. 18), and the refractive index distribution image ((c) in FIG. 18) are superimposed.

FIG. 18 includes diagrams for describing an eighth analysis example in the analysis step S3. (a) in FIG. 18 is a diagram schematically showing the refractive index variation image acquired by labeling the specific component in each of the cells included in the cell mass with the labeling substance α. (b) in FIG. 18 is a diagram schematically showing the refractive index variation image acquired by labeling the other specific component in each of the cells included in the cell mass with the other labeling substance β. (c) in FIG. 18 is a diagram schematically showing the refractive index distribution image. (d) in FIG. 18 is a diagram in which the refractive index variation image ((a) in FIG. 18), the refractive index variation image ((b) in FIG. 18), and the refractive index distribution image ((c) in FIG. 18) are superimposed.

In the eighth analysis example, it is possible to know a region in which the cells each including the specific components respectively labeled with the labeling substances α and β are present in the cell mass, and for example, it is possible to know that the cells each including the specific component labeled with the labeling substance α are present in a peripheral region, and further, the cells each including the specific component labeled with the labeling substance β are present in a center region.

Next, examples will be described. The optical module 30 was attached to a camera port of a differential interference contrast microscope (ECLIPSE Ti-2) manufactured by Nikon Corporation to constitute the cell evaluation apparatus 1 (FIG. 2), and by using the above apparatus, the phase image of the cell in which the specific component was labeled with the labeling substance was acquired, and further, the refractive index distribution image and the refractive index variation image were obtained. Depending on the type of the labeling substance, the light of any two wavelengths out of 433±12 nm, 530±21.5 nm, 620±26 nm, and 694±22 nm was used to acquire the phase image. By combining a light emitting diode and a bandpass filter manufactured by Semrock, the light of each wavelength was selected and output.

As the labeling substance, brilliant cresyl blue, new methylene blue, janus green B (the above three types of the labeling substances were purchased from Muto Pure Chemicals) and neutral red (purchased from Sigma-Aldrich) were used. As the cell of the evaluation object, the human lung cancer derived A549 cell line and the human liver cancer derived HepG2 cell line were used.

FIG. 19 is a table showing the labeling substances, the center wavelengths, and the cells used in the respective examples. This table also shows the center wavelengths and the cells for comparative examples 3 and 4 in which the labeling substance was not used.

The brilliant cresyl blue used in the examples 1A and 1B is one of vital staining dyes (basic dyes), is known to be taken up into the cell by endocytosis (pinocytosis), and further, is also known as a staining dye for the nucleolus. The new methylene blue used in the examples 2A and 2B is known to have a property similar to that of the brilliant cresyl blue.

The neutral red used in the example 3 is one of vital staining dyes, and is used for cell uptake assay. The uptake of the neutral red is related to maintenance of ATP dependent pH gradient. The ianus green B used in the example 4 is one of vital staining dyes, and is known to stain the mitochondrion in blue, and further, is also known to stain other various proteins. Further, the janus green B is known to stain the cell nucleus and the cytoplasm in the cultured cell.

The light absorption spectrum of the labeling substance was measured using a spectrophotometer U-4100 manufactured by Hitachi, Ltd. The refractive index spectrum of the labeling substance was estimated from the light absorption spectrum based on the Kramers-Kronig relations.

Figure 20:
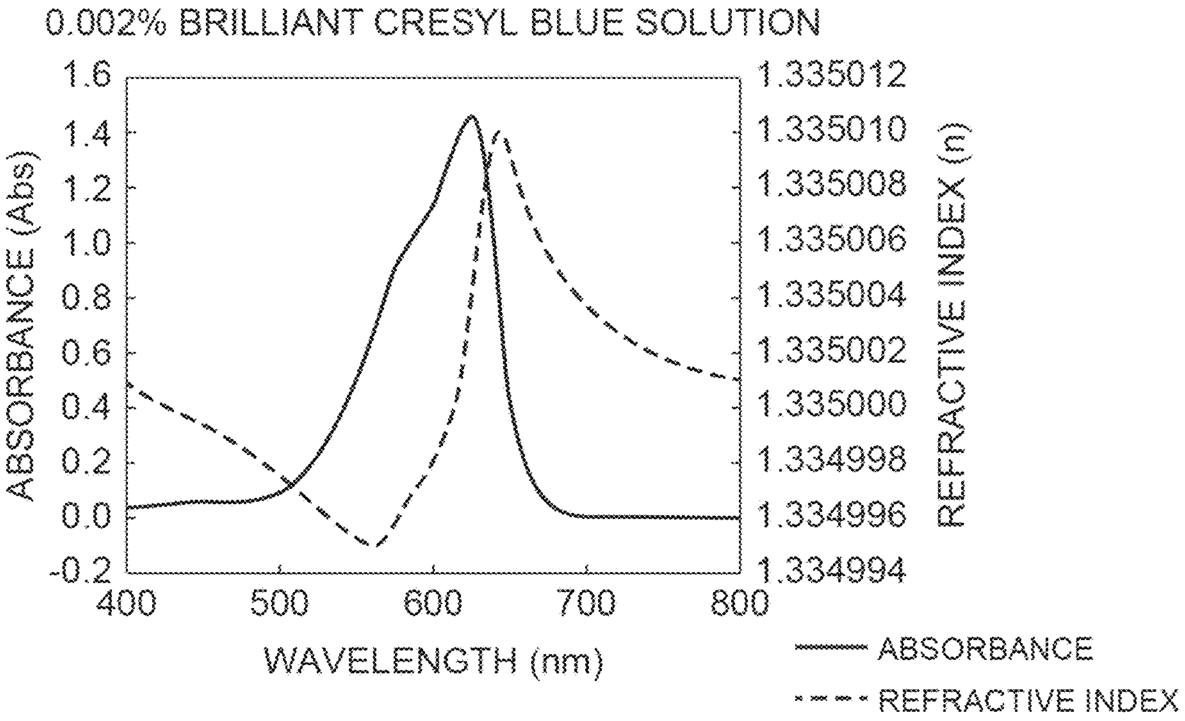
FIG. 20 is a graph showing a measured light absorption spectrum and an estimated refractive index spectrum of a 0.002% brilliant cresyl blue solution.
Figure 21:
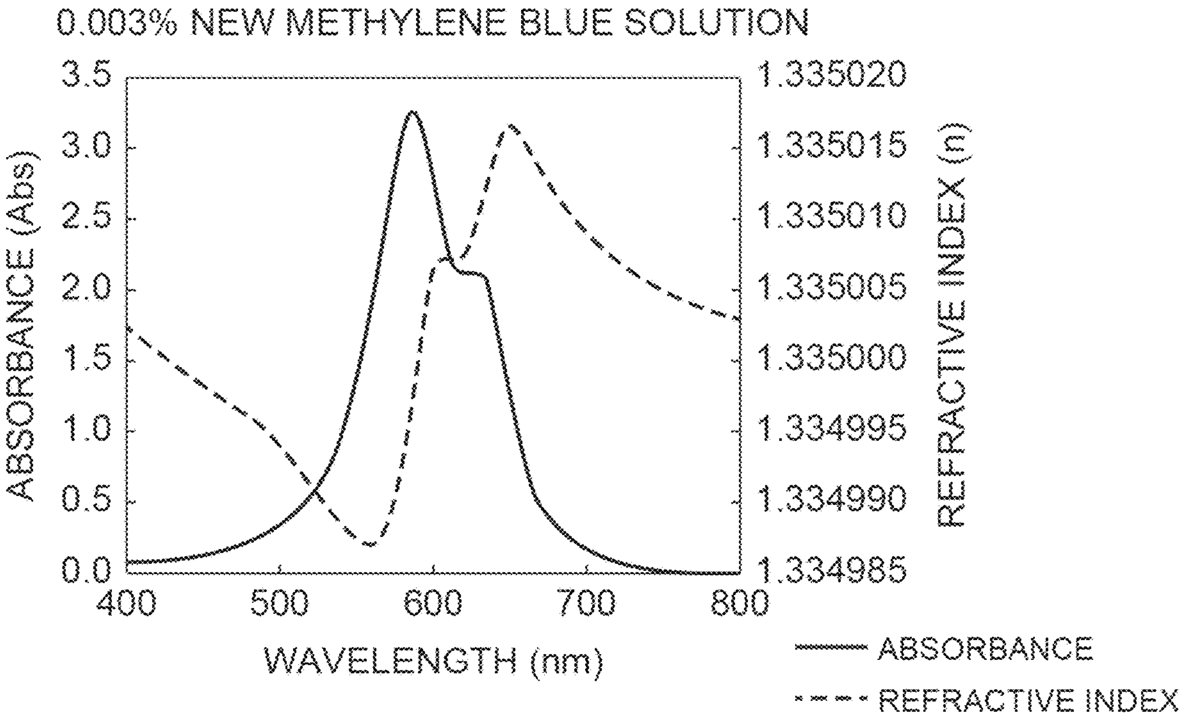
FIG. 21 is a graph showing a measured light absorption spectrum and an estimated refractive index spectrum of a 0.003% new methylene blue solution.
Figure 22:
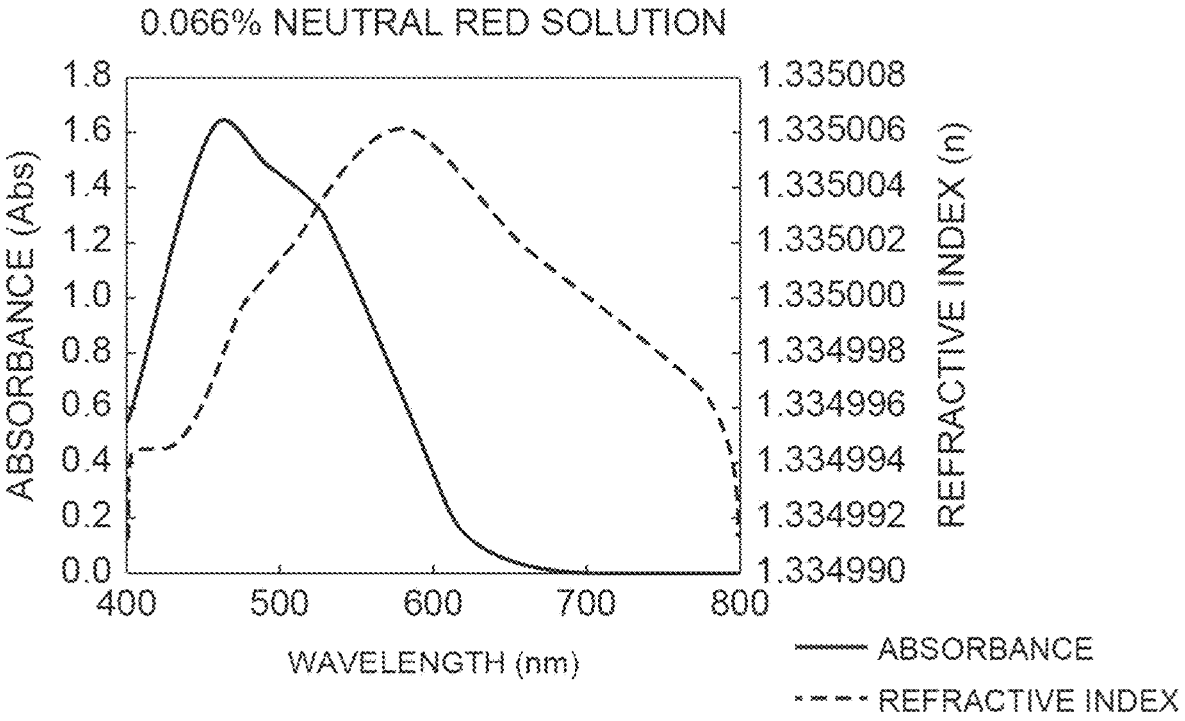
FIG. 22 is a graph showing a measured light absorption spectrum and an estimated refractive index spectrum of a 0.066% neutral red solution.
Figure 23:
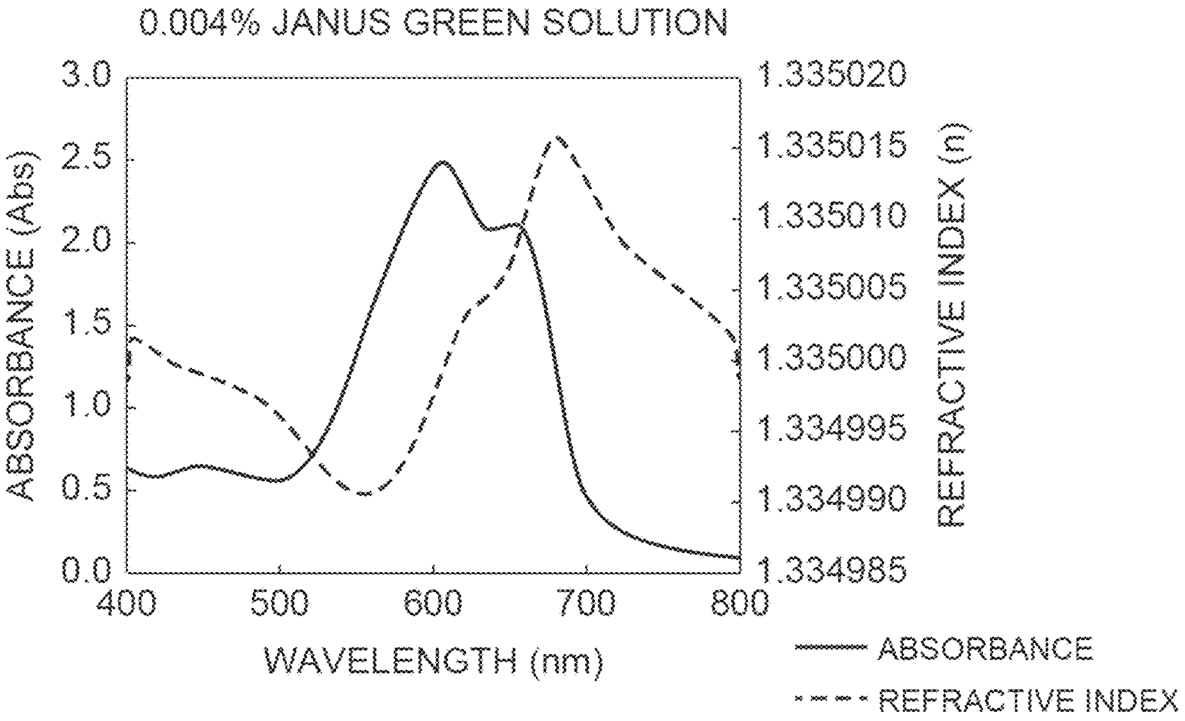
FIG. 23 is a graph showing a measured light absorption spectrum and an estimated refractive index spectrum of a 0.004% janus green B solution.

FIG. 20 is a graph showing a measured light absorption spectrum and an estimated refractive index spectrum of a 0.002% brilliant cresyl blue solution. FIG. 21 is a graph showing a measured light absorption spectrum and an estimated refractive index spectrum of a 0.003% new methylene blue solution. FIG. 22 is a graph showing a measured light absorption spectrum and an estimated refractive index spectrum of a 0.066% neutral red solution. FIG. 23 is a graph showing a measured light absorption spectrum and an estimated refractive index spectrum of a 0.004% janus green B solution. Based on the above refractive index profiles, the first wavelength and the second wavelength of the light used at the time of the measurement of the refractive index distribution were set as shown in FIG. 19.

FIG. 24 to FIG. 27 include respective images of the example 1A. In the example 1A, the brilliant cresyl blue was used as the labeling substance, the light of the center wavelength of each of 433 nm and 694 nm was used when the refractive index distribution was measured, and the A549 cell line was used as the cell of the evaluation object.

(a) in FIG. 24 is the phase image at the center wavelength of 433 nm. (b) in FIG. 24 is the phase image at the center wavelength of 694 nm. A position indicated by an arrow (a) in the diagram is a component labeled with the labeling substance, in which the phase is 1.51 and the refractive index is 1.354 at the center wavelength of 433 nm, the phase is 2.05 and the refractive index is 1.378 at the center wavelength of 694 nm, and the refractive index is high at the longer wavelength. In addition, the value of the refractive index was estimated assuming that a thickness of the cell was 5 μm and a refractive index of a background medium was 1.333.

A position indicated by an arrow (b) in the diagram is a component not labeled with the labeling substance, in which the phase is 1.52 and the refractive index is 1.354 at the center wavelength of 433 nm, the phase is 0.72 and the refractive index is 1.349 at the center wavelength of 694 nm, and the refractive index is low at the longer wavelength.

(a) in FIG. 25 is the refractive index distribution image at the center wavelength of 433 nm. (b) in FIG. 25 is the refractive index distribution image at the center wavelength of 694 nm. The above refractive index distribution images are generated by correcting each pixel value of the phase image based on the wavelength. The refractive index distribution image of (a) in FIG. 25 is obtained by multiplying the phase image of (a) in FIG. 24 by a coefficient of 4.33. The refractive index distribution image of (b) in FIG. 25 is obtained by multiplying the phase image of (b) in FIG. 24 by a coefficient of 6.94. The value of the coefficient by which each phase image is multiplied may be a value that is a fixed multiple of the wavelength of the light used at the time of the acquisition of the phase image.

(a) in FIG. 26 is an enlarged diagram of a range indicated by a dashed line rectangle in (a) in FIG. 25. (b) in FIG. 26 is an enlarged diagram of a range indicated by a dashed line rectangle in (b) in FIG. 25. (a) in FIG. 27 is the intensity image at the center wavelength of 530 nm. (b) in FIG. 27 is the refractive index variation image generated from (a) in FIG. 26 and (b) in FIG. 26.

The refractive index variation image ((b) in FIG. 27) is obtained by subtracting the refractive index distribution image at the center wavelength of 433 nm ((a) in FIG. 26) from the refractive index distribution image at the center wavelength of 694 nm ((b) in FIG. 26), and extracting a region in which the phase is larger than the background (phase 0) (a region in which the phase has a positive value). In addition, the refractive index variation image may be generated based on the ratio of the refractive index distribution images at the two wavelengths, or may be generated based on the comparison between the difference or the ratio of the refractive index distribution images at the two wavelengths and a threshold value. When the intensity image ((a) in FIG. 27) and the refractive index variation image ((b) in FIG. 27) are compared, it can be seen that the component labeled with the labeling substance is detected as the variation of the refractive index.

Figure 28:
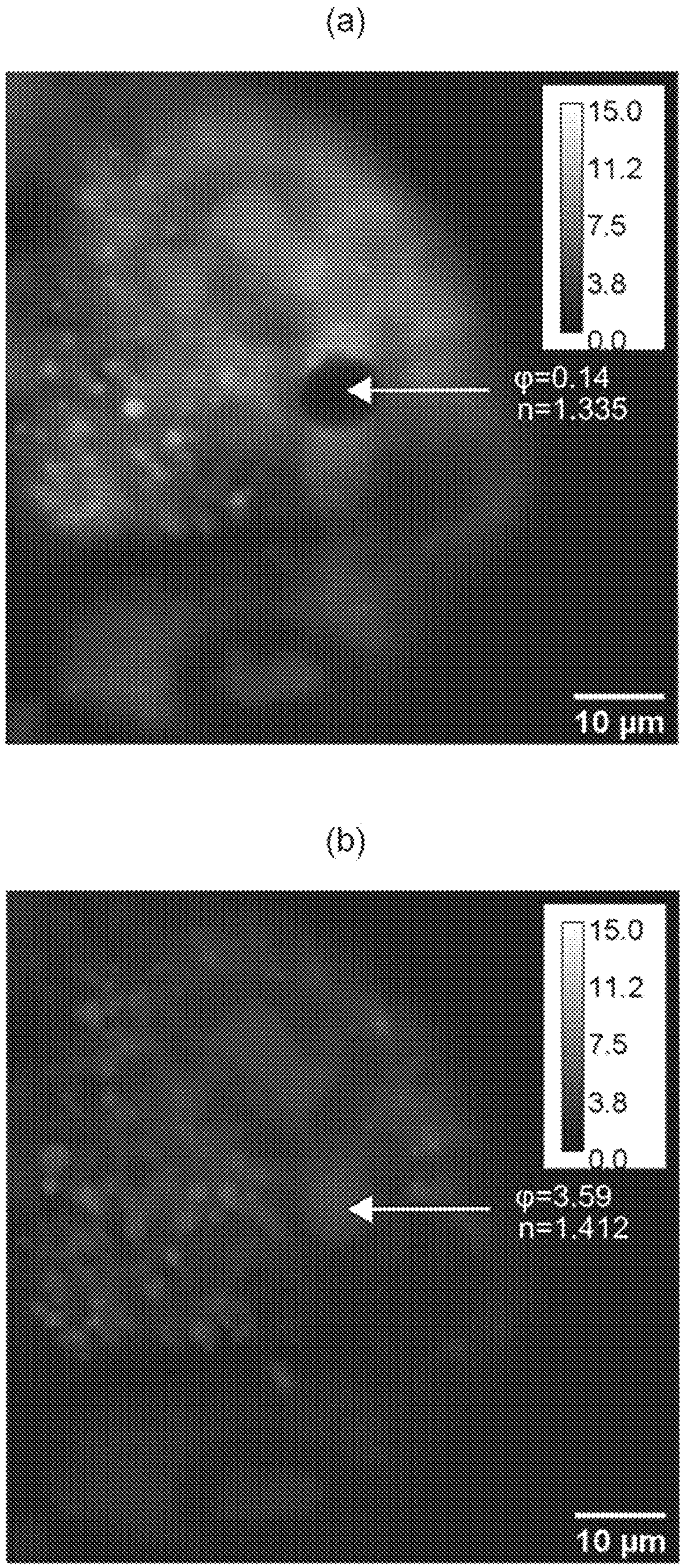
FIG. 28 includes respective images of an example 1B, and shows (a) the phase image at the center wavelength of 433 nm, and (b) the phase image at the center wavelength of 694 nm.

FIG. 28 and FIG. 29 include respective images of the example 1B. In the example 1B, the brilliant cresyl blue was used as the labeling substance, the light of the center wavelength of each of 433 nm and 694 nm was used when the refractive index distribution was measured, and the HepG2 cell line was used as the cell of the evaluation object.

(a) in FIG. 28 is the phase image at the center wavelength of 433 nm. (b) in FIG. 28 is the phase image at the center wavelength of 694 nm. A position indicated by an arrow in the diagram is a component labeled with the labeling substance, in which the phase is 0.14 and the refractive index is 1.335 at the center wavelength of 433 nm, the phase is 3.59 and the refractive index is 1.412 at the center wavelength of 694 nm, and the refractive index is high at the longer wavelength.

(a) in FIG. 29 is the intensity image at the center wavelength of 530 nm. (b) in FIG. 29 is the refractive index variation image. The refractive index variation image ((b) in FIG. 29) is generated in the same manner as in the example 1A. When the intensity image ((a) in FIG. 29) and the refractive index variation image ((b) in FIG. 29) are compared, it can be seen that, also in the example 1B, as in the example 1A, the component labeled with the labeling substance is detected as the variation of the refractive index.

FIG. 30 and FIG. 31 include respective images of the example 2A. In the example 2A, the new methylene blue was used as the labeling substance, the light of the center wavelength of each of 530 nm and 694 nm was used when the refractive index distribution was measured, and the A549 cell line was used as the cell of the evaluation object.

(a) in FIG. 30 is the phase image at the center wavelength of 530 nm. (b) in FIG. 30 is the phase image at the center wavelength of 694 nm. (a) in FIG. 31 is the intensity image at the center wavelength of 530 nm. (b) in FIG. 31 is the refractive index variation image. The refractive index variation image ((b) in FIG. 31) is generated in the same manner as in the example 1A. When the intensity image ((a) in FIG. 31) and the refractive index variation image ((b) in FIG. 31) are compared, it can be seen that, also in the example 2A, similarly, the component labeled with the labeling substance is detected as the variation of the refractive index.

Figure 33:
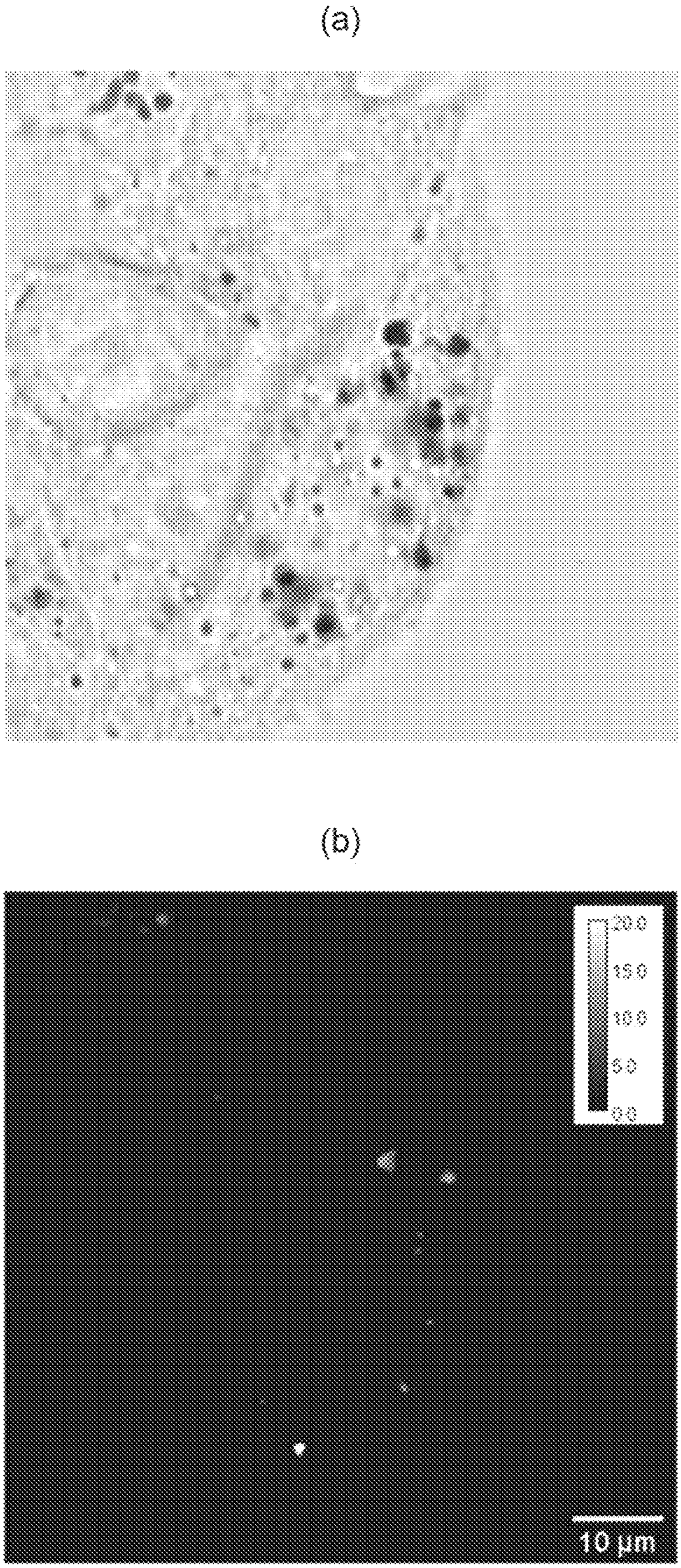
FIG. 33 includes respective images of the example 2B, and shows (a) the intensity image at the center wavelength of 530 nm, and (b) the refractive index variation image.

FIG. 32 and FIG. 33 include respective images of the example 2B. In the example 2B, the new methylene blue was used as the labeling substance, the light of the center wavelength of each of 530 nm and 694 nm was used when the refractive index distribution was measured, and the HepG2 cell line was used as the cell of the evaluation object.

(a) in FIG. 32 is the phase image at the center wavelength of 530 nm. (b) in FIG. 32 is the phase image at the center wavelength of 694 nm. (a) in FIG. 33 is the intensity image at the center wavelength of 530 nm. (b) in FIG. 33 is the refractive index variation image. The refractive index variation image ((b) in FIG. 33) is generated in the same manner as in the example 1A. When the intensity image ((a) in FIG. 33) and the refractive index variation image ((b) in FIG. 33) are compared, it can be seen that, also in the example 2B, similarly, the component labeled with the labeling substance is detected as the variation of the refractive index.

FIG. 34 and FIG. 35 include respective images of the example 3. In the example 3, the neutral red was used as the labeling substance, the light of the center wavelength of each of 433 nm and 620 nm was used when the refractive index distribution was measured, and the HepG2 cell line was used as the cell of the evaluation object.

(a) in FIG. 34 is the phase image at the center wavelength of 433 nm. (b) in FIG. 34 is the phase image at the center wavelength of 620 nm. (a) in FIG. 35 is the intensity image at the center wavelength of 530 nm. (b) in FIG. 35 is the refractive index variation image. The refractive index variation image ((b) in FIG. 35) is generated in the same manner as in the example 1A. When the intensity image ((a) in FIG. 35) and the refractive index variation image ((b) in FIG. 35) are compared, it can be seen that, also in the example 3, similarly, the component labeled with the labeling substance is detected as the variation of the refractive index.

FIG. 36 and FIG. 37 include respective images of the comparative example 3. The comparative example 3 is different from the example 3 in that the labeling substance was not used.

(a) in FIG. 36 is the phase image at the center wavelength of 433 nm. (b) in FIG. 36 is the phase image at the center wavelength of 620 nm. (a) in FIG. 37 is the intensity image at the center wavelength of 530 nm. (b) in FIG. 37 is the refractive index variation image. The refractive index variation image ((b) in FIG. 37) is generated in the same manner as in the example 1A. In the comparative example 3 in which the labeling substance is not used, the specific component in the cell is hardly detected.

FIG. 38 and FIG. 39 include respective images of the example 4. In the example 4, the janus green B was used as the labeling substance, the light of the center wavelength of each of 530 nm and 694 nm was used when the refractive index distribution was measured, and the A549 cell line was used as the cell of the evaluation object.

(a) in FIG. 38 is the phase image at the center wavelength of 530 nm. (b) in FIG. 38 is the phase image at the center wavelength of 694 nm. (a) in FIG. 39 is the intensity image at the center wavelength of 530 nm. (b) in FIG. 39 is the refractive index variation image. The refractive index variation image ((b) in FIG. 39) is generated in the same manner as in the example 1A. When the intensity image ((a) in FIG. 39) and the refractive index variation image ((b) in FIG. 39) are compared, it can be seen that, also in the example 4, similarly, the component labeled with the labeling substance is detected as the variation of the refractive index.

FIG. 40 and FIG. 41 include respective images of the comparative example 4. The comparative example 4 is different from the example 4 in that the labeling substance was not used.

(a) in FIG. 40 is the phase image at the center wavelength of 530 nm. (b) in FIG. 40 is the phase image at the center wavelength of 694 nm. (a) in FIG. 41 is the intensity image at the center wavelength of 530 nm. (b) in FIG. 41 is the refractive index variation image. The refractive index variation image ((b) in FIG. 41) is generated in the same manner as in the example 1A. In the comparative example 4 in which the labeling substance is not used, the specific component in the cell is hardly detected.

As described above, in the present embodiment, the specific component in the cell is labeled with the labeling substance having the refractive indices different from each other respectively at the first wavelength and the second wavelength, the refractive index distribution of the cell is acquired at each of the first wavelength and the second wavelength, and the refractive index distributions respectively at the first wavelength and the second wavelength are compared to evaluate the distribution of the specific component in the cell. According to the present embodiment, it is possible to easily evaluate the cell even in the case in which the cell in an unknown cell.

In the intensity image ((a) in FIG. 27 and the like) also, the distribution of the specific component labeled with the labeling substance can be obtained. However, the intensity image is affected not only by light absorption due to the labeling substance but also by light scattering and the like. In the intensity image, decrease in the light intensity may be observed not only due to the influence of absorption but also due to refraction or scattering of the light at the boundary between structures having different refractive indices (this may also be observed in an unlabeled cell).

The influence of the light scattering and the like may cause noise. This is a problem even in the intensity image at one wavelength, but may also be a problem in the case of comparing the intensity images at a plurality of wavelengths. On the other hand, in the refractive index distribution image, the refractive index can be quantified, and thus, the above problem can be easily avoided. Therefore, in the refractive index variation image, noise caused by the light scattering and the like can be reduced.

In the case in which the light absorbing labeling substance is used, the light is less likely to be transmitted in a wavelength region having the light absorption (a region near the predetermined wavelength $\lambda_0$) in (a) in FIG. 5), which may affect the acquisition of the refractive index distribution image. When the cell mass is observed by the ODT using the light from a plurality of directions, the above influence is expected to increase, and it becomes difficult to observe a deep portion.

However, in the refractive index spectrum of the light absorbing labeling substance, by setting the first wavelength and the second wavelength in the vicinity of the wavelength at which the refractive index has the local minimum on the short wavelength side with respect to the predetermined wavelength $\lambda_0$ or in the vicinity of the wavelength at which the refractive index has the local maximum on the long wavelength side with respect to the predetermined wavelength $\lambda_0$ ((b) in FIG. 5 and FIG. 6), the phase image or the refractive index distribution image can be acquired by using the light having the wavelength with small light absorption.

Further, in the case in which the light absorbing labeling substance is used, the first wavelength and the second wavelength which are relatively close to each other can be set ((b) in FIG. 5 and FIG. 6). By comparing the refractive index distribution images at the first wavelength and the second wavelength which are relatively close to each other, extraction of the refractive index variation image becomes easy, and data with a high SN ratio can be obtained.

On the assumption that the refractive index distribution images are acquired with the light of the plurality of wavelengths, by comparing a case in which the object component is identified using the intensity image at the wavelength (hereinafter, referred to as a "case 1"), and a case in which the object component is identified using the refractive index distribution images at the plurality of wavelengths (hereinafter, referred to as a "case 2"), the following can be said.

In the case 2, in the case in which the low refractive index peak (the first wavelength) and the high refractive index peak (the second wavelength) are relatively close to each other, by comparing the refractive index distribution images at the first wavelength and the second wavelength, the extraction of the refractive index variation region becomes easy, and there is an advantage that data with a high SN ratio is easily obtained. This is because, in the case 2, it is possible to capture a large variation of the refractive index distribution of the labeled component in a situation in which the variation of the refractive index distribution of the unlabeled component is small, which is an advantage over the case 1.

On the other hand, even in the case in which the low refractive index peak (the first wavelength) and the high refractive index peak (the second wavelength) are not relatively close to each other due to the light absorption spectrum and the refractive index spectrum of the labeling substance, in the case 2, it is assumed that the low refractive index peak is clear in the refractive index spectrum in many cases, and therefore, by comparing the refractive index distribution images at the first wavelength and the second wavelength, the extraction of the refractive index variation region becomes easy, and data with a high SN ratio can be easily obtained.

The above advantage of the case 2 with respect to the case 1 is due to the fact that, in the case 1, it is necessary to pay attention to the high absorbance peak in the light absorption spectrum, and on the other hand, in the case 2, attention is paid to the low refractive index peak in addition to the high refractive index peak in the refractive index spectrum.

In the case in which the fluorescence image is acquired, it is necessary to perform irradiation with excitation light with high power, and thus there are problems of phototoxicity and photobleaching. On the other hand, in the present embodiment, it is not necessary to perform irradiation with light with high power, and thus the problems of the phototoxicity and the photobleaching are minimized, and time lapse observation of the cells for a long time can be performed. Further, since the problem of the phototoxicity is minimized, observation can be performed in the state in which the original function of the cell is maintained, and further, since the problem of the photobleaching is minimized, quantitative observation can be performed.

Further, in the case in which the light absorbing labeling substance is used, when the irradiation is performed with the light in the wavelength region having the light absorption (the region near the predetermined wavelength $\lambda_0$ in (a) in FIG. 5), the energy of the absorbed light may be converted into heat or the like, which may cause cytotoxicity. On the other hand, in the present embodiment, the wavelength region having the light absorption can be avoided ((b) in FIG. 5), and thus, it is possible to perform observation in the state in which the cytotoxicity is reduced and the original function of the cell is maintained.

Further, the refractive index distribution image and the refractive index variation image can be acquired by using the one apparatus, and further, the intensity image ((a) in FIG. 27 and the like) can also be acquired. By comparing the refractive index variation image and the intensity image of the cell, it is possible to perform biologically meaningful observation.

In addition, in the present embodiment, the absolute value of the refractive index is obtained, and thus, observation excellent in quantitativeness can be performed as compared with the case in which only the intensity image is acquired. Further, the light absorbing labeling substance suitable for the labeling may be screened according to the present embodiment.

The cell evaluation method and the cell evaluation apparatus are not limited to the embodiments and configuration examples described above, and various other modifications are possible.

The cell evaluation method according to the above embodiment includes a labeling step of labeling a specific component in a cell with a labeling substance having refractive indices different from each other respectively at a first wavelength and a second wavelength; a refractive index distribution acquisition step of acquiring a refractive index distribution of the cell in which the specific component is labeled in the labeling step at each of the first wavelength and the second wavelength; and an analysis step of evaluating a distribution of the specific component in the cell by comparing the refractive index distributions respectively at the first wavelength and the second wavelength.

In the above cell evaluation method, in the labeling step, the specific component in the cell may be labeled with the labeling substance having a higher refractive index at a longer wavelength out of the first wavelength and the second wavelength than a refractive index at a shorter wavelength. Further, in the labeling step, the specific component in the cell may be labeled with the labeling substance having a lower refractive index at a longer wavelength out of the first wavelength and the second wavelength than a refractive index at a shorter wavelength.

In the above cell evaluation method, in the labeling step, the specific component in the cell may be labeled with a light absorbing labeling substance having an absorption peak at a predetermined wavelength, and in the refractive index distribution acquisition step, the refractive index distribution of the cell in which the specific component is labeled in the labeling step may be acquired at each of the first wavelength and the second wavelength set on a short wavelength side or a long wavelength side with respect to the predetermined wavelength.

In the above cell evaluation method, in the labeling step, the specific component in the cell may be labeled with a light absorbing labeling substance having an absorption peak at a predetermined wavelength, and in the refractive index distribution acquisition step, the refractive index distribution of the cell in which the specific component is labeled in the labeling step may be acquired at each of the first wavelength and the second wavelength, with one wavelength out of the first wavelength and the second wavelength set on a short wavelength side with respect to the predetermined wavelength and another wavelength set on a long wavelength side with respect to the predetermined wavelength.

In the above cell evaluation method, in the labeling step, a construct for intracellular expression in which a DNA sequence encoding a chromoprotein is connected to a N-terminus or a C-terminus of a DNA sequence encoding an arbitrary protein may be introduced into the cell, and the specific component may be labeled with the construct for intracellular expression used as the labeling substance.

In the above cell evaluation method, in the analysis step, the distribution of the specific component in the cell may be evaluated based on a ratio or a difference between the refractive index distributions respectively at the first wavelength and the second wavelength. Further, in the analysis step, analysis of the specific component in the cell may be performed by superimposing a comparison result of the refractive index distributions respectively at the first wavelength and the second wavelength on an intensity image or a fluorescence image of the cell.

In the above cell evaluation method, in the labeling step, another specific component in the cell may be labeled with another labeling substance having refractive indices respectively at a third wavelength and a fourth wavelength different from each other, in the refractive index distribution acquisition step, a refractive index distribution of the cell labeled in the labeling step may be acquired at each of the third wavelength and the fourth wavelength, and in the analysis step, a distribution of the another specific component in the cell may be evaluated by comparing the refractive index distributions respectively at the third wavelength and the fourth wavelength. Further, in this case, the first wavelength or the second wavelength may be equal to the third wavelength or the fourth wavelength.

The cell evaluation apparatus according to the above embodiment includes a refractive index distribution acquisition unit for acquiring a refractive index distribution of a cell in which a specific component is labeled with a labeling substance having refractive indices different from each other respectively at a first wavelength and a second wavelength at each of the first wavelength and the second wavelength; and an analysis unit for evaluating a distribution of the specific component in the cell by comparing the refractive index distributions respectively at the first wavelength and the second wavelength.

The program according to the above embodiment is a program for causing a computer to execute a refractive index distribution acquisition step of acquiring a refractive index distribution of a cell in which a specific component is labeled with a labeling substance having refractive indices different from each other respectively at a first wavelength and a second wavelength at each of the first wavelength and the second wavelength; and an analysis step of evaluating a distribution of the specific component in the cell by comparing the refractive index distributions respectively at the first wavelength and the second wavelength.

INDUSTRIAL APPLICABILITY

The embodiments can be used as a cell evaluation method and a cell evaluation apparatus capable of easily evaluating a cell even in the case in which the cell is an unknown cell.

REFERENCE SIGNS LIST

1, 2A, 2B—cell evaluation apparatus, 10—refractive index distribution acquisition unit, 11—light source, 12—lens, 13—polarizer, 14—first prism, 15—condenser lens, 21—objective lens, 22—second prism, 24—lens, 27—mirror, 30—optical module, 31—lens, 33—quarter wave plate, 34—lens, 35—polarization camera, 36-38—mirror, 39—operation unit, 40—analysis unit, 50A, 50B—refractive index distribution acquisition unit, 51, 52—laser light source, 53, 54—shutter, 55—mirror, 56—dichroic mirror, 57—beam splitter, 61, 62—lens, 63, 64—optical fiber, 71—lens, 72—mirror, 73—lens, 74—condenser lens, 75—objective lens, 81—beam splitter, 82—lens, 83A, 83B—camera, 84—operation unit, 90—analysis unit.

The invention claimed is:

1. A cell evaluation method comprising:

performing a labeling of labeling a specific component in a cell with a labeling substance having refractive indices respectively at a first wavelength and a second wavelength different from each other;

performing a refractive index distribution acquisition of acquiring a refractive index distribution of the cell in which the specific component is labeled in the labeling at each of the first wavelength and the second wavelength; and performing an analysis of evaluating a distribution of the specific component in the cell by comparing the refractive index distributions respectively at the first wavelength and the second wavelength.

2. The cell evaluation method according to claim 1, wherein in the labeling, the specific component in the cell is labeled with the labeling substance having a higher refractive index at a longer wavelength out of the first wavelength and the second wavelength than a refractive index at a shorter wavelength.

3. The cell evaluation method according to claim 1, wherein in the labeling, the specific component in the cell is labeled with the labeling substance having a lower refractive index at a longer wavelength out of the first wavelength and the second wavelength than a refractive index at a shorter wavelength.

4. The cell evaluation method according to claim 1, wherein in the labeling, the specific component in the cell is labeled with a light absorbing labeling substance having an absorption peak at a predetermined wavelength, and in the refractive index distribution acquisition, the refractive index distribution of the cell in which the specific component is labeled in the labeling is acquired at each of the first wavelength and the second wavelength set on a short wavelength side or a long wavelength side with respect to the predetermined wavelength.

5. The cell evaluation method according to claim 1, wherein in the labeling, the specific component in the cell is labeled with a light absorbing labeling substance having an absorption peak at a predetermined wavelength, and in the refractive index distribution acquisition, the refractive index distribution of the cell in which the specific component is labeled in the labeling is acquired at each of the first wavelength and the second wavelength, with one wavelength out of the first wavelength and the second wavelength set on a short wavelength side with respect to the predetermined wavelength and another wavelength set on a long wavelength side with respect to the predetermined wavelength.

6. The cell evaluation method according to claim 1, wherein in the labeling, a construct for intracellular expression in which a DNA sequence encoding a chromoprotein is connected to a N-terminus or a C-terminus of a DNA sequence encoding an arbitrary protein is introduced into the cell, and the specific component is labeled with the construct for intracellular expression used as the labeling substance.

7. The cell evaluation method according to claim 1, wherein in the analysis, the distribution of the specific component in the cell is evaluated based on a ratio or a difference between the refractive index distributions respectively at the first wavelength and the second wavelength.

8. The cell evaluation method according to claim 1, wherein in the analysis, analysis of the specific component in the cell is performed by superimposing a comparison result of the refractive index distributions respectively at the first wavelength and the second wavelength on an intensity image or a fluorescence image of the cell.

9. The cell evaluation method according to claim 1, wherein in the labeling, another specific component in the cell is labeled with another labeling substance having refractive indices respectively at a third wavelength and a fourth wavelength different from each other, in the refractive index distribution acquisition, a refractive index distribution of the cell labeled in the labeling is acquired at each of the third wavelength and the fourth wavelength, and in the analysis, a distribution of the another specific component in the cell is evaluated by comparing the refractive index distributions respectively at the third wavelength and the fourth wavelength.

10. The cell evaluation method according to claim 9, wherein the first wavelength or the second wavelength is equal to the third wavelength or the fourth wavelength.

11. A cell evaluation apparatus comprising:

a refractive index distribution acquisition unit configured to acquire a refractive index distribution of a cell in which a specific component is labeled with a labeling substance having refractive indices respectively at a first wavelength and a second wavelength different from each other at each of the first wavelength and the second wavelength; and an analysis unit configured to evaluate a distribution of the specific component in the cell by comparing the refractive index distributions respectively at the first wavelength and the second wavelength.

12. A non-transitory computer-readable storage media storing a program for causing a computer to execute:

performing a refractive index distribution acquisition of acquiring a refractive index distribution of a cell in which a specific component is labeled with a labeling substance having refractive indices respectively at a first wavelength and a second wavelength different from each other at each of the first wavelength and the second wavelength; and performing an analysis of evaluating a distribution of the specific component in the cell by comparing the refractive index distributions respectively at the first wavelength and the second wavelength.

* * * * *